US010244926B2

(12) United States Patent
Noonan et al.

(10) Patent No.: US 10,244,926 B2
(45) Date of Patent: Apr. 2, 2019

(54) DETECTING ENDOLUMENAL BUCKLING OF FLEXIBLE INSTRUMENTS

(71) Applicant: Auris Health, Inc., Redwood City, CA (US)

(72) Inventors: David P. Noonan, San Carlos, CA (US); Don A. Tanaka, Saratoga, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 15/392,917

(22) Filed: Dec. 28, 2016

(65) Prior Publication Data

US 2018/0177383 A1    Jun. 28, 2018

(51) Int. Cl.
*A61B 1/005* (2006.01)
*A61B 34/30* (2016.01)
(Continued)

(52) U.S. Cl.
CPC .......... *A61B 1/0051* (2013.01); *A61B 1/0016* (2013.01); *A61B 1/00055* (2013.01);
(Continued)

(58) Field of Classification Search
CPC .............. A61B 1/0051; A61B 1/00133; A61B 1/00149; A61B 1/0016; A61B 34/30;
(Continued)

(56) References Cited

U.S. PATENT DOCUMENTS

| 4,644,237 A | 2/1987 | Frushour et al. |
| 4,748,969 A * | 6/1988 | Wardle ................ A61B 1/0051 138/120 |

(Continued)

FOREIGN PATENT DOCUMENTS

| DE | 102013100605 | 7/2014 |
| EP | 1 566 150 | 8/2005 |

(Continued)

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.
(Continued)

*Primary Examiner* — John P Leubecker
(74) *Attorney, Agent, or Firm* — Knobbe Martens Olson & Bear LLP

(57) ABSTRACT

A robotic system is described for determining whether a flexible instrument has buckled. The robotic system comprises a medical instrument comprising an elongate body, and further comprises a first sensor placed in a first portion of the elongate body, and a controller. A command is directed to the elongate body. The first sensor generates sensor data providing information regarding a first measured status of the portion of the elongate body. The controller receives sensor data generated from the first sensor, and compare the first measured status with a first expected status expected to be caused by the command; and responsive to the first measured status deviating from the first expected status one of more or less than a first associated threshold, determine that the elongate body has buckled.

30 Claims, 32 Drawing Sheets

(51) Int. Cl.
*A61B 1/00* (2006.01)
*A61B 1/05* (2006.01)
*A61B 5/06* (2006.01)
*A61B 34/00* (2016.01)
*A61B 34/37* (2016.01)

(52) U.S. Cl.
CPC .............. *A61B 1/051* (2013.01); *A61B 5/065* (2013.01); *A61B 34/30* (2016.02); *A61B 34/74* (2016.02); *A61B 34/76* (2016.02); *A61B 34/37* (2016.02); *A61B 2034/301* (2016.02); *A61B 2034/304* (2016.02); *A61B 2034/742* (2016.02); *A61B 2034/743* (2016.02)

(58) Field of Classification Search
CPC ... A61B 2034/301; A61B 34/37; A61B 34/70; A61B 5/065
See application file for complete search history.

(56) References Cited

U.S. PATENT DOCUMENTS

| | | | |
|---|---|---|---|
| 5,280,781 | A | 1/1994 | Oku |
| 5,408,263 | A | 4/1995 | Kikuchi |
| 5,672,877 | A | 9/1997 | Liebig et al. |
| 5,899,851 | A | 5/1999 | Koninckx |
| 6,004,016 | A | 12/1999 | Spector |
| 6,198,974 | B1 | 3/2001 | Webster, Jr. |
| 6,246,200 | B1 | 6/2001 | Blumenkranz et al. |
| 6,459,926 | B1 | 10/2002 | Nowlin |
| 6,837,846 | B2 * | 1/2005 | Jaffe ............... A61B 1/0008 600/114 |
| 7,197,354 | B2 | 3/2007 | Sobe |
| 7,607,440 | B2 | 10/2009 | Coste-Maniere et al. |
| 7,772,541 | B2 | 8/2010 | Froggatt et al. |
| 8,335,557 | B2 | 12/2012 | Maschke |
| 8,396,595 | B2 | 3/2013 | Dariush |
| 8,442,618 | B2 | 5/2013 | Strommer et al. |
| 8,506,555 | B2 | 8/2013 | Ruiz Morales |
| 8,554,368 | B2 | 10/2013 | Fielding et al. |
| 8,720,448 | B2 | 5/2014 | Reis et al. |
| 8,738,181 | B2 | 5/2014 | Greer et al. |
| 8,827,948 | B2 | 9/2014 | Romo et al. |
| 8,929,631 | B2 | 1/2015 | Pfister et al. |
| 8,945,095 | B2 | 2/2015 | Blumenkranz |
| 9,014,851 | B2 | 4/2015 | Wong et al. |
| 9,129,417 | B2 | 9/2015 | Zheng et al. |
| 9,199,372 | B2 | 12/2015 | Henderson et al. |
| 9,226,796 | B2 | 1/2016 | Bowling |
| 9,256,940 | B2 | 2/2016 | Carelsen et al. |
| 9,289,578 | B2 | 3/2016 | Walker et al. |
| 9,314,306 | B2 * | 4/2016 | Yu ............... A61B 6/12 |
| 9,345,456 | B2 | 5/2016 | Tsonton et al. |
| 9,358,682 | B2 | 6/2016 | Ruiz Morales |
| 9,504,604 | B2 | 11/2016 | Alvarez |
| 9,561,083 | B2 | 2/2017 | Yu et al. |
| 9,622,827 | B2 | 4/2017 | Yu et al. |
| 9,629,595 | B2 | 4/2017 | Walker et al. |
| 9,636,184 | B2 | 5/2017 | Lee et al. |
| 9,675,422 | B2 | 6/2017 | Hourtash et al. |
| 9,713,509 | B2 | 7/2017 | Schuh et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,789,608 | B2 | 10/2017 | Ltkowitz et al. |
| 9,818,681 | B2 | 11/2017 | MacHida |
| 9,844,353 | B2 | 12/2017 | Walker et al. |
| 9,844,412 | B2 | 12/2017 | Bogusky et al. |
| 9,867,635 | B2 | 1/2018 | Alvarez et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 2002/0161280 | A1 | 10/2002 | Chatenever et al. |
| 2003/0045778 | A1 | 3/2003 | Ohline |
| 2003/0182091 | A1 | 9/2003 | Kukuk |
| 2004/0257021 | A1 | 12/2004 | Chang et al. |
| 2005/0043718 | A1 | 2/2005 | Madhani |
| 2005/0065400 | A1 | 3/2005 | Banik |
| 2005/0256398 | A1 * | 11/2005 | Hastings ............... A61B 34/73 600/423 |
| 2005/0261551 | A1 | 11/2005 | Couvillon |
| 2006/0015096 | A1 | 1/2006 | Hauck et al. |
| 2006/0041293 | A1 | 2/2006 | Mehdizadeh |
| 2007/0013336 | A1 | 1/2007 | Nowlin et al. |
| 2007/0043455 | A1 * | 2/2007 | Viswanathan ......... A61B 90/36 700/66 |
| 2007/0135886 | A1 | 6/2007 | Maschke |
| 2007/0150155 | A1 | 6/2007 | Kawai |
| 2007/0249911 | A1 | 10/2007 | Simon |
| 2007/0253599 | A1 | 11/2007 | White et al. |
| 2007/0287992 | A1 | 12/2007 | Diolaiti |
| 2007/0299353 | A1 | 12/2007 | Harley et al. |
| 2008/0046122 | A1 | 2/2008 | Manzo et al. |
| 2008/0108870 | A1 | 5/2008 | Wiita et al. |
| 2008/0123921 | A1 | 5/2008 | Gielen et al. |
| 2008/0140087 | A1 | 6/2008 | Barbagli et al. |
| 2008/0159653 | A1 | 7/2008 | Dunki-Jacobs et al. |
| 2008/0231221 | A1 | 9/2008 | Ogawa |
| 2008/0249640 | A1 | 10/2008 | Vittor et al. |
| 2008/0255505 | A1 | 10/2008 | Carlson et al. |
| 2008/0312771 | A1 | 12/2008 | Sugiura |
| 2009/0076534 | A1 | 3/2009 | Shelton |
| 2009/0184825 | A1 | 7/2009 | Anderson |
| 2009/0198298 | A1 | 8/2009 | Kaiser et al. |
| 2009/0245600 | A1 | 10/2009 | Hoffman |
| 2009/0287354 | A1 | 11/2009 | Choi |
| 2010/0030115 | A1 * | 2/2010 | Fujimoto ......... A61B 17/12022 600/587 |
| 2010/0076263 | A1 | 3/2010 | Tanaka |
| 2010/0121138 | A1 | 5/2010 | Goldenberg et al. |
| 2010/0234856 | A1 | 9/2010 | Stoianovici et al. |
| 2010/0256812 | A1 | 10/2010 | Tsusaka et al. |
| 2011/0082462 | A1 | 4/2011 | Suarez |
| 2011/0137122 | A1 | 6/2011 | Kawai |
| 2011/0153252 | A1 * | 6/2011 | Govari ............... A61B 5/1495 702/98 |
| 2011/0160570 | A1 * | 6/2011 | Kariv ............... A61B 5/721 600/424 |
| 2011/0196199 | A1 | 8/2011 | Donhowe et al. |
| 2011/0319910 | A1 | 12/2011 | Roelle et al. |
| 2012/0000427 | A1 | 1/2012 | Nilsson |
| 2012/0046522 | A1 | 2/2012 | Naito |
| 2012/0059249 | A1 | 3/2012 | Verard et al. |
| 2012/0071752 | A1 | 3/2012 | Sewell |
| 2012/0071822 | A1 | 3/2012 | Romo et al. |
| 2012/0123441 | A1 | 5/2012 | Au |
| 2012/0209293 | A1 | 8/2012 | Carlson |
| 2012/0215094 | A1 | 8/2012 | Rahimian et al. |
| 2012/0253276 | A1 | 10/2012 | Govari et al. |
| 2012/0328077 | A1 | 12/2012 | Bouvier |
| 2013/0090530 | A1 | 4/2013 | Ramamurthy |
| 2013/0102846 | A1 | 4/2013 | Sjostrom |
| 2013/0131503 | A1 | 5/2013 | Schneider et al. |
| 2013/0165854 | A1 | 6/2013 | Sandhu et al. |
| 2013/0165945 | A9 | 6/2013 | Roelle |
| 2013/0325030 | A1 | 12/2013 | Hourtash et al. |
| 2014/0114180 | A1 | 4/2014 | Jain |
| 2014/0135985 | A1 | 5/2014 | Coste-Maniere et al. |
| 2014/0142591 | A1 | 5/2014 | Alvarez et al. |
| 2014/0163664 | A1 | 6/2014 | Goldsmith |
| 2014/0222207 | A1 | 8/2014 | Bowling et al. |
| 2014/0296870 | A1 | 10/2014 | Stern et al. |
| 2014/0309649 | A1 | 10/2014 | Alvarez et al. |
| 2014/0316420 | A1 | 10/2014 | Ballard et al. |
| 2014/0357984 | A1 | 12/2014 | Wallace et al. |
| 2014/0364870 | A1 | 12/2014 | Alvarez et al. |

(56) References Cited

U.S. PATENT DOCUMENTS

| | | |
|---|---|---|
| 2014/0379000 A1 | 12/2014 | Romo et al. |
| 2015/0051592 A1 | 2/2015 | Kintz |
| 2015/0088161 A1 | 3/2015 | Hata |
| 2015/0101442 A1 | 4/2015 | Romo |
| 2015/0104284 A1 | 4/2015 | Riedel |
| 2015/0119628 A1 | 4/2015 | Bharat et al. |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164596 A1 | 6/2015 | Romo |
| 2015/0202015 A1 | 7/2015 | Elhawary |
| 2015/0223902 A1 | 8/2015 | Walker et al. |
| 2015/0265359 A1 | 9/2015 | Camarillo |
| 2015/0265807 A1 | 9/2015 | Park et al. |
| 2015/0297864 A1* | 10/2015 | Kokish .............. A61M 25/0113 604/95.04 |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0081568 A1 | 3/2016 | Kolberg |
| 2016/0100772 A1* | 4/2016 | Ikuma .................... A61B 5/065 600/424 |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287111 A1 | 10/2016 | Jacobsen |
| 2016/0287279 A1 | 10/2016 | Bovay et al. |
| 2016/0296294 A1 | 10/2016 | Moll et al. |
| 2016/0331469 A1 | 11/2016 | Hall et al. |
| 2016/0338787 A1 | 11/2016 | Popovic |
| 2016/0346924 A1 | 12/2016 | Hasegawa |
| 2016/0354057 A1 | 12/2016 | Hansen et al. |
| 2016/0360949 A1 | 12/2016 | Hyodo |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0068796 A1 | 3/2017 | Passerini et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0151027 A1* | 6/2017 | Walker ................... A61B 34/37 |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0251988 A1 | 9/2017 | Weber et al. |
| 2017/0280978 A1* | 10/2017 | Yamamoto ......... A61B 1/00167 |
| 2017/0281049 A1* | 10/2017 | Yamamoto ............. A61B 5/065 |
| 2017/0290631 A1 | 10/2017 | Lee et al. |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |

FOREIGN PATENT DOCUMENTS

| | | |
|---|---|---|
| EP | 1 800 593 | 6/2007 |
| EP | 2 158 834 | 3/2010 |
| EP | 3 025 630 | 6/2016 |
| WO | WO 01/56457 | 8/2001 |
| WO | WO 06/122061 | 11/2006 |
| WO | WO 09/120940 | 10/2009 |
| WO | WO 11/132409 | 10/2011 |
| WO | WO 17/048194 | 3/2017 |

OTHER PUBLICATIONS

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

International Search Report and Written Opinion in application No. PCT/US2017/068535, dated May 18, 2018.

* cited by examiner

500

```
┌─────────────────────────────────────────────┐
│ Receive a sample of images captured by an   │
│ image sensor of an endoscope.               │
│ 510                                         │
└─────────────────────────────────────────────┘
                      │
                      ▼
┌─────────────────────────────────────────────┐
│ Generate a difference array for a pair of   │
│ images of the sample.                       │
│ 520                                         │
└─────────────────────────────────────────────┘
                      │
                      ▼
┌─────────────────────────────────────────────┐
│ Generate a gradient array for the pair of   │
│ images of the sample.                       │
│ 530                                         │
└─────────────────────────────────────────────┘
                      │
                      ▼
┌─────────────────────────────────────────────┐
│ Determine a motion of the endoscope based   │
│ on the generated difference array and       │
│ gradient array                              │
│ 540                                         │
└─────────────────────────────────────────────┘
```

FIG. 5A

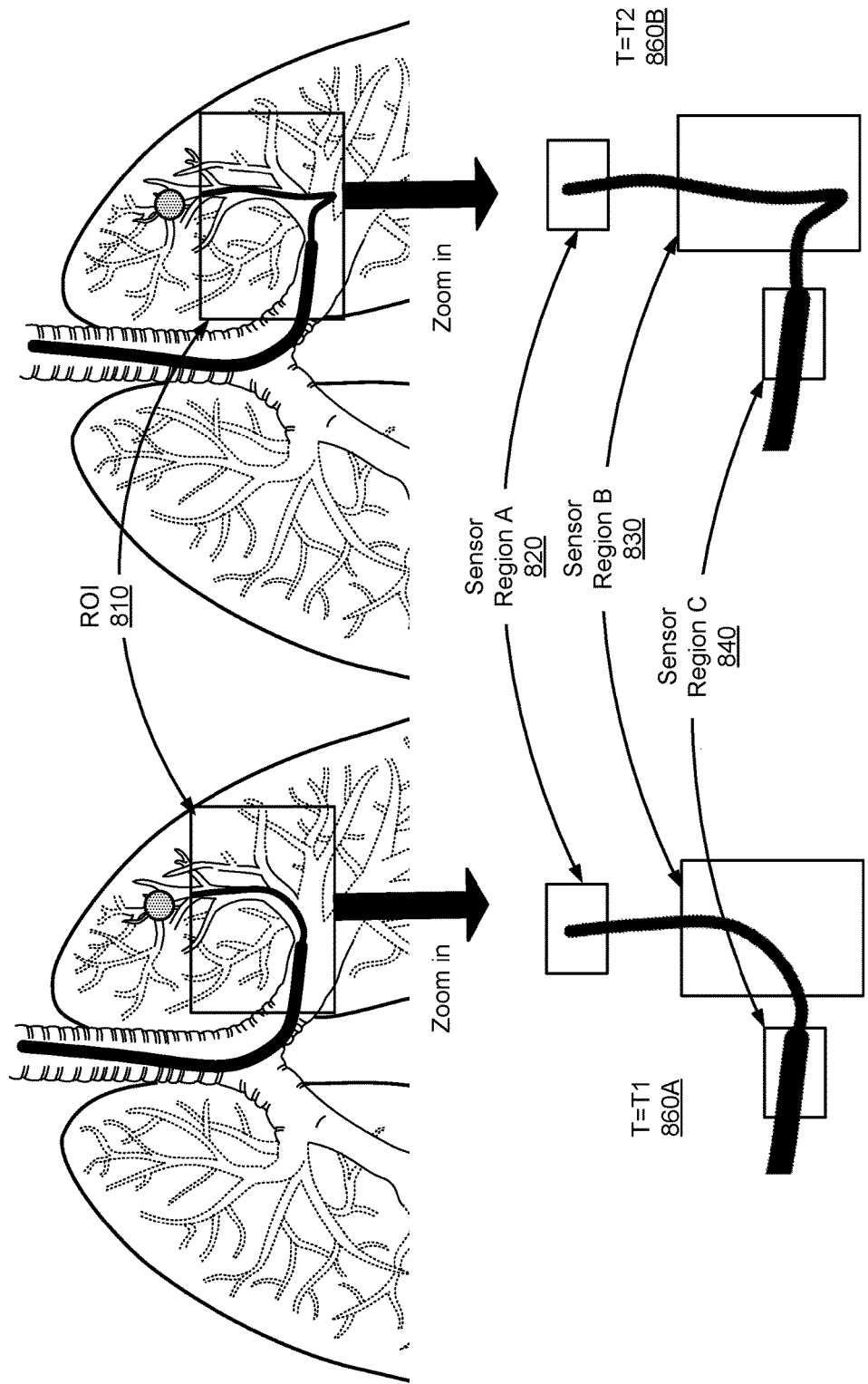

Measured Status            Expected Status
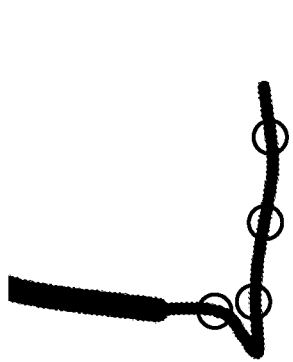 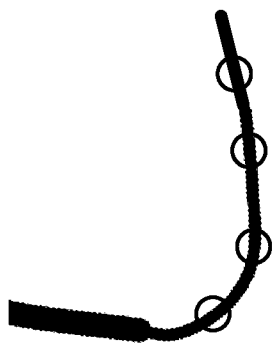
FIG. 9I            FIG. 9J
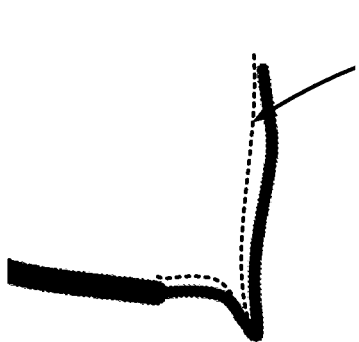 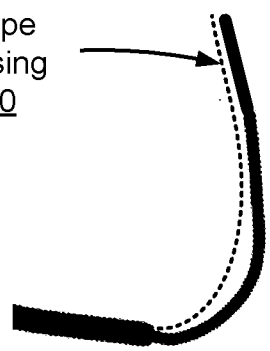
Shape Sensing 950
FIG. 9K            FIG. 9L

1000

Receive sensor data generated from a first sensor placed in a portion of the endoscope located within a patient lumen, the sensor data indicating a measured status based on an actual motion of the portion of the endoscope
1010

Receive expected data describing data associated with an expected status caused by an expected motion of the endoscope
1020

Compare the measured status with the expected status
1030

Responsive to the measured status deviating from the expected status more or less than an associated threshold, determine that the endoscope has buckled
1040

FIG. 10

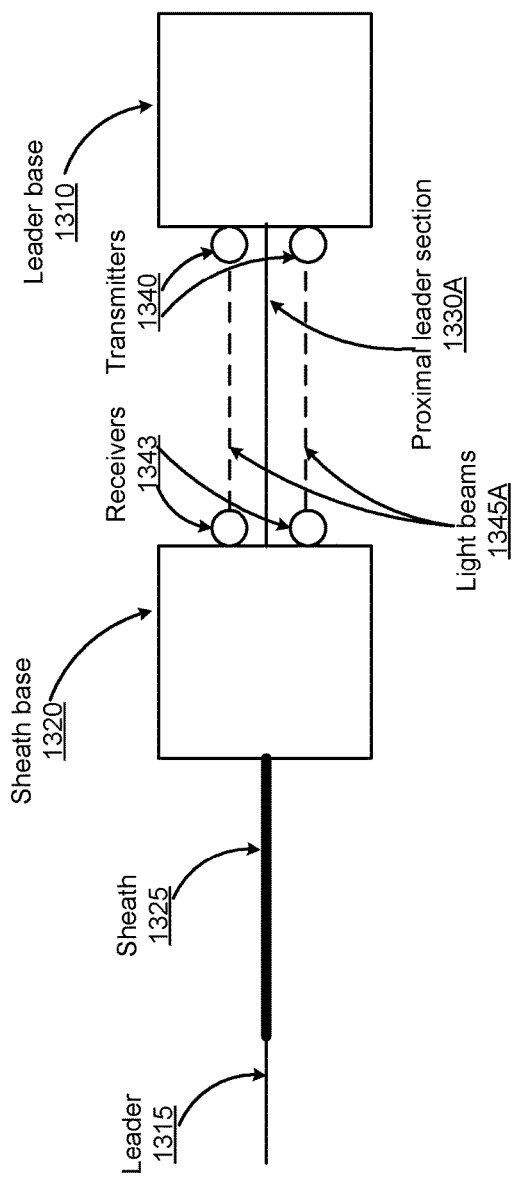
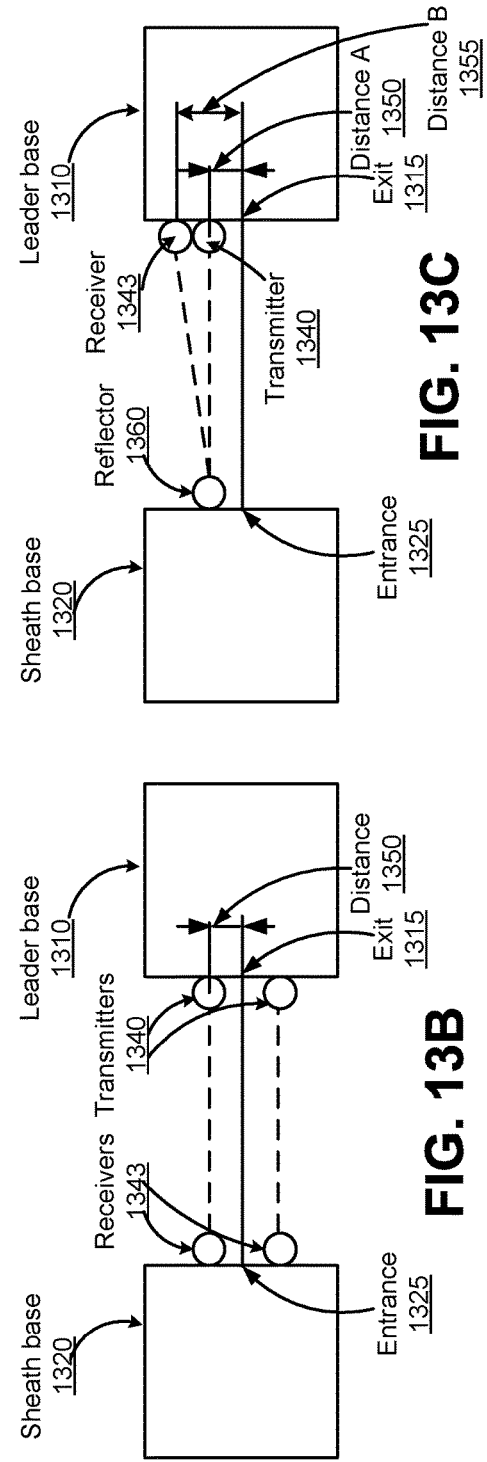
FIG. 13A
FIG. 13B
FIG. 13C

1400

Provide one or more commands to a surgical robotic system to move the endoscope
1410

Receive receiver data generated from at least one transmitter-receiver pair placed along a length of the endoscope outside the patient, the transmitter-receiver pair configured to transmit a light beam from a transmitter to a receiver, the receiver data indicating whether the receiver has had received light beam transmitted from the transmitter
1420

Responsive to the receiver data indicating that the light from the from the transmitter has been blocked, determine that the endoscope has buckled
1430

FIG. 14

DETECTING ENDOLUMENAL BUCKLING OF FLEXIBLE INSTRUMENTS

CROSS REFERENCE TO RELATED APPLICATIONS

This application is related to U.S. patent application Ser. No. 15/392,868, entitled "FLEXIBLE INSTRUMENT INSERTION USING AN ADAPTIVE INSERTION FORCE THRESHOLD," filed on an even date herewith, which is incorporated herein by reference in its entirety for all purposes.

BACKGROUND

1. Field of Art

This description generally relates to surgical robotics, and particularly to controlling insertion of a surgical instrument into an anatomical lumen of a patient.

2. Description of the Related Art

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians and/or surgeons have started using robotic arms to help perform surgical procedures. For instance, physicians and/or surgeons use robotic arms to control surgical instruments such as endoscopes.

An endoscope is able to perform surgical procedures in a minimally invasive manner. The endoscope can be directed to a target location of a patient, such as the lung or blood vessel. The robotic arms applies a force to insert the endoscope into an open access point of a patient, e.g., mouth, anus, urethra, to the target location within the patient lumen. As the endoscope is inserted deeper into the patient anatomy, the endoscope may brush, rub, and push against internal anatomy that may be fragile and subject to tearing if too much insertion force is applied. Moreover, during the endoscope moves to the target location, the endoscope typically may buckle in response to slack or insertion insistence in the endoscope and incidental force from coming in contact with patient anatomy. When the endoscope buckles, the physicians and/or surgeons continue to push the scope, and increase insertion force beyond normal levels in order to advance the endoscope. This creates a danger of the buckled portion of the endoscope storing up undesirable potential energy, which may be potentially unwound in an uncontrollable way within the patient lumen/cavity or damage the endoscope.

SUMMARY

The present disclosure describes a flexible instrument having one or more sensors placed on one or more portions of an elongate body of the flexible instrument to detect buckling. The one or more sensors may be of the same or different types. As commands are directed to the elongate body, sensor data captured from the one or more sensors are compared with data expected to be received in response to the commands to determine if buckling has occurred.

Other aspects include methods, components, devices, systems, improvements, methods, processes, applications, computer readable mediums, and other technologies related to any of the above.

BRIEF DESCRIPTION OF DRAWINGS

FIG. 5A is a flowchart of a process for determining movements of an endoscope from a sequence of recorded images according to one embodiment.

FIGS. 8A and 8B illustrate examples of sensor regions used to place sensors according to one embodiment.

FIGS. 9A-9L illustrate examples of endolumenal buckling detection based on a comparison between measured status and expected status according to one embodiment.

FIG. 10 is a flowchart of a process for detecting endolumenal buckling based on a comparison between measured status and expected status according to one embodiment.

FIGS. 13A-13F are examples of detecting buckling of an endoscope outside a patient according to one embodiment.

FIG. 14 is a flowchart of a process for detecting buckling outside a patient based using transmitter-receiver pairs according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Robotic Flexible Instrument System Basics

The methods and apparatus disclosed herein are well suited for use with one or more endoscope components or steps as described in U.S. application. Ser. No. 14/523,760, filed on Oct. 24, 2014, published as U.S. Pat. Pub. No. US 2015/0119637, entitled "SYSTEM FOR ROBOTIC-ASSISTED ENDOLUMENAL SURGERY AND RELATED METHODS," the full disclosure of which is incorporated herein by reference. The aforementioned application describes system components, endolumenal systems, virtual rail configurations, mechanism changer interfaces, instrument device manipulators (IDMs), endoscope tool designs, control consoles, endoscopes, instrument device manipulators, endolumenal navigation, and endolumenal procedures suitable for combination in accordance with embodiments disclosed herein. The principles described in the above application are also applicable to catheter designs. Generally, although the following sections of this description describe endoscope embodiments, this is merely one example, and the description that follows can also be implemented and/or used in conjunction with catheters as well, or more generally any flexible instrument comprising an elongate body.

I.A Surgical Robotic System

Figure 1A:
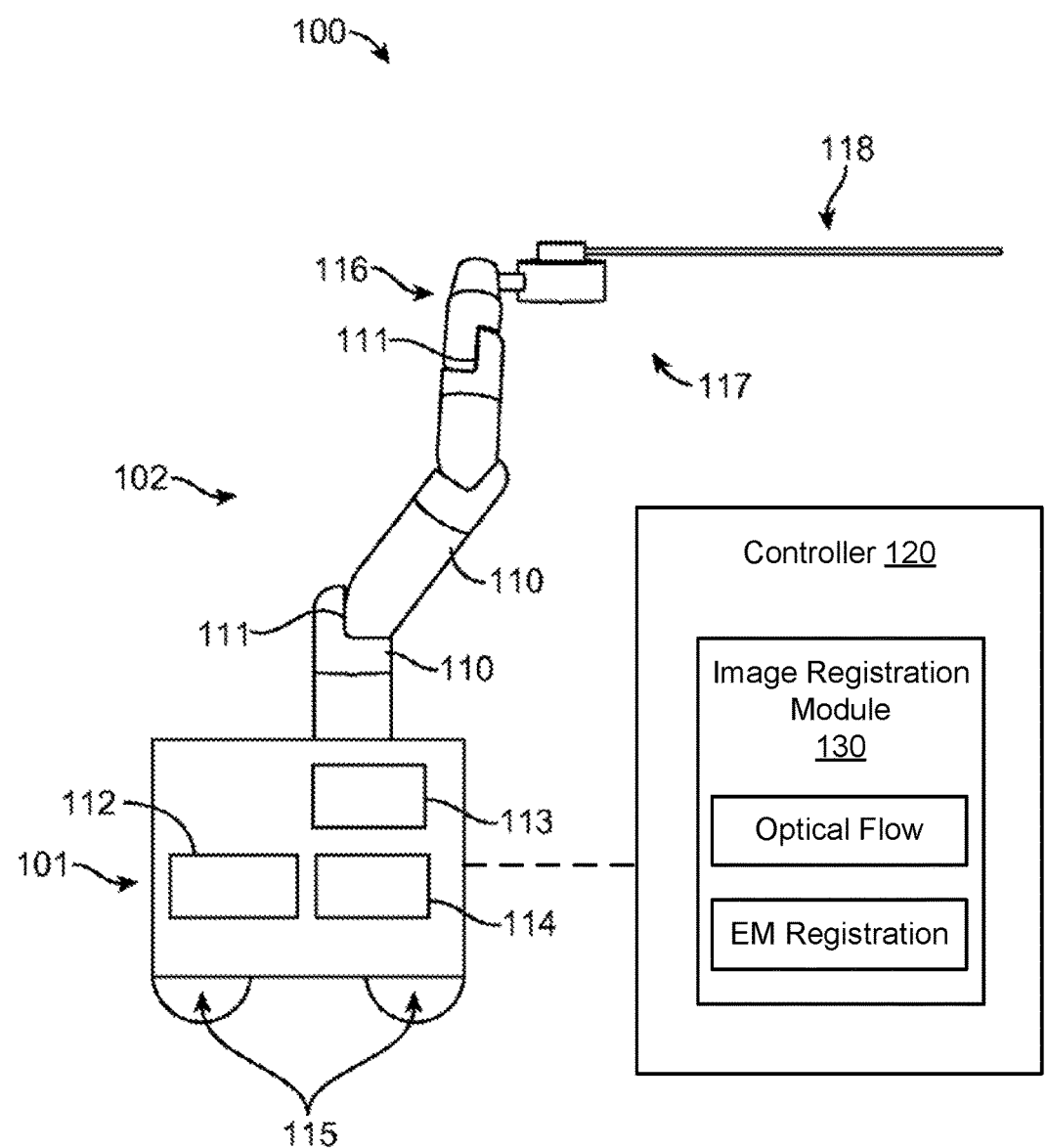
FIG. 1A illustrates a surgical robotic system according to one embodiment.

FIG. 1A illustrates a surgical robotic system 100 according to one embodiment. The surgical robotic system 100 includes a base 101 coupled to one or more robotic arms, e.g., robotic arm 102. The base 101 is communicatively coupled to a command console, which is further described with reference to FIG. 2 in Section I.B. Command Console. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic arm 102 can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-3C in Section I.C. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

The surgical robotic system 100 includes a controller 120, for example, a computer processor. The controller 120 includes image registration module 130, and a store 135. The surgical robotic system 100 uses the image registration module 130 for determining movement of the endoscope, which is further described in Section I.C.2. Optical Flow and I.C.3. EM Registration. In some embodiments, some or all functionality of the controller 120 is performed outside the surgical robotic system 100, for example, on another computer system or server communicatively coupled to the surgical robotic system 100.

Figure 1B:
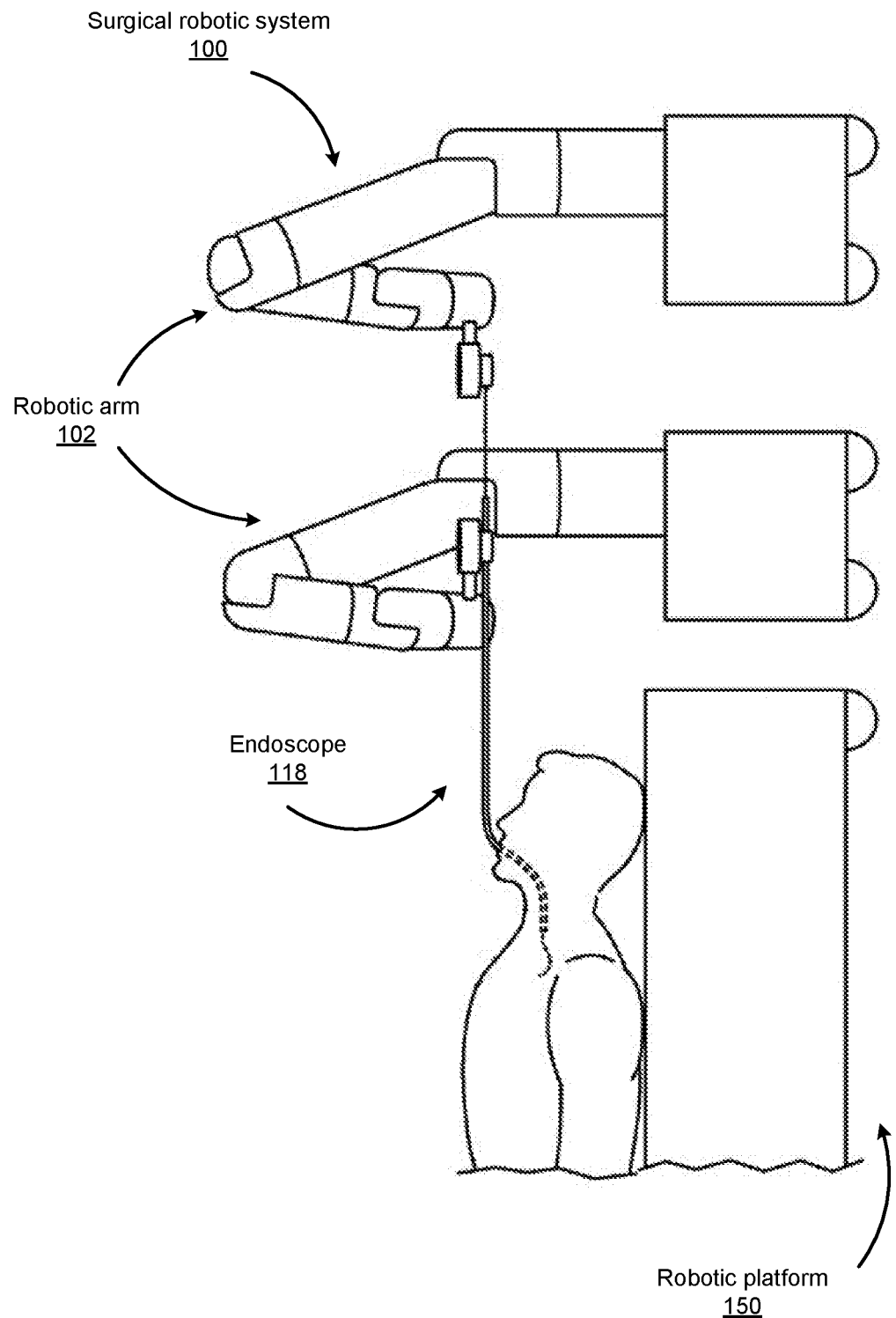
FIGS. 1B-1F show various perspective views of a robotic platform coupled to the surgical robotic system shown in FIG. 1A, according to one embodiment.
Figure 1C:
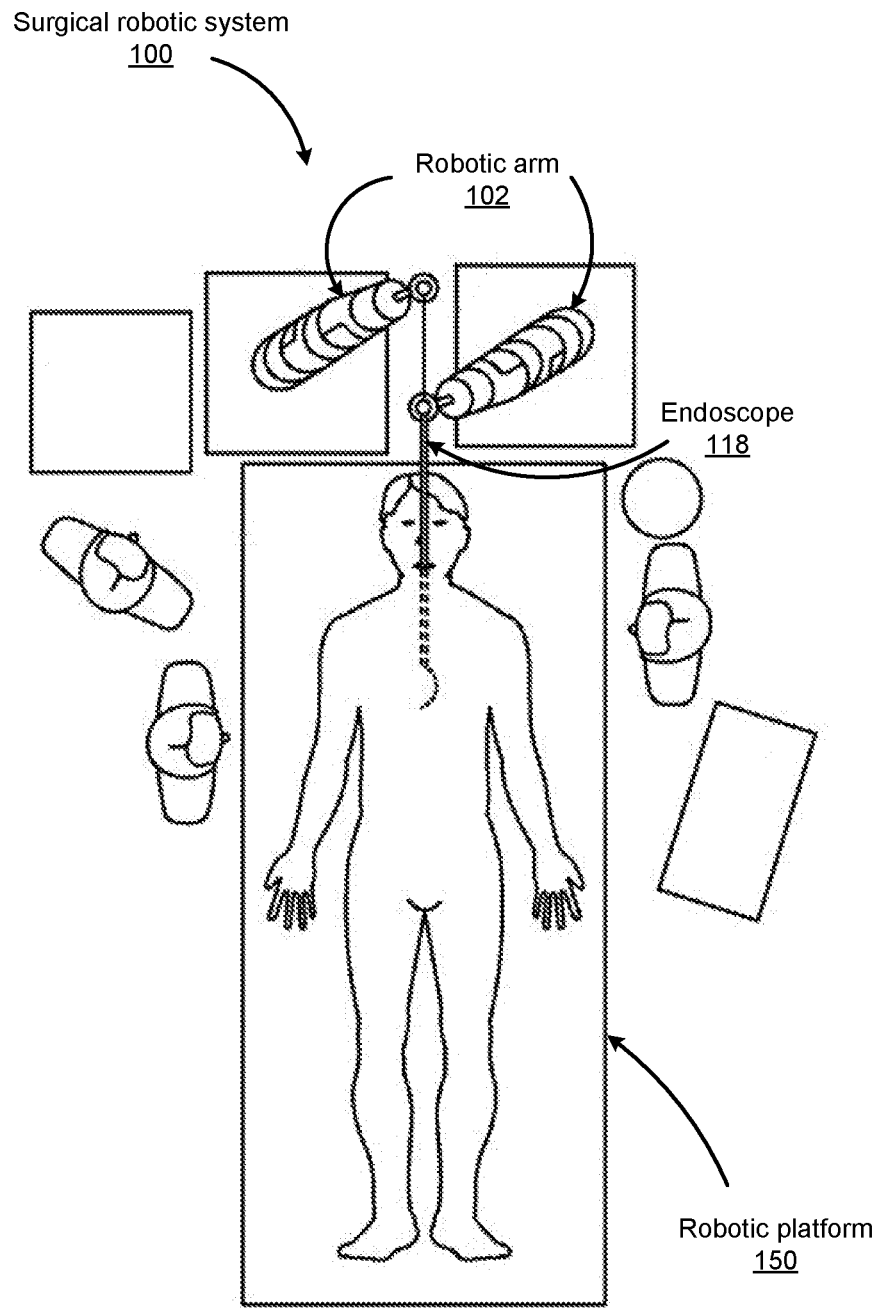
Figure 1D:
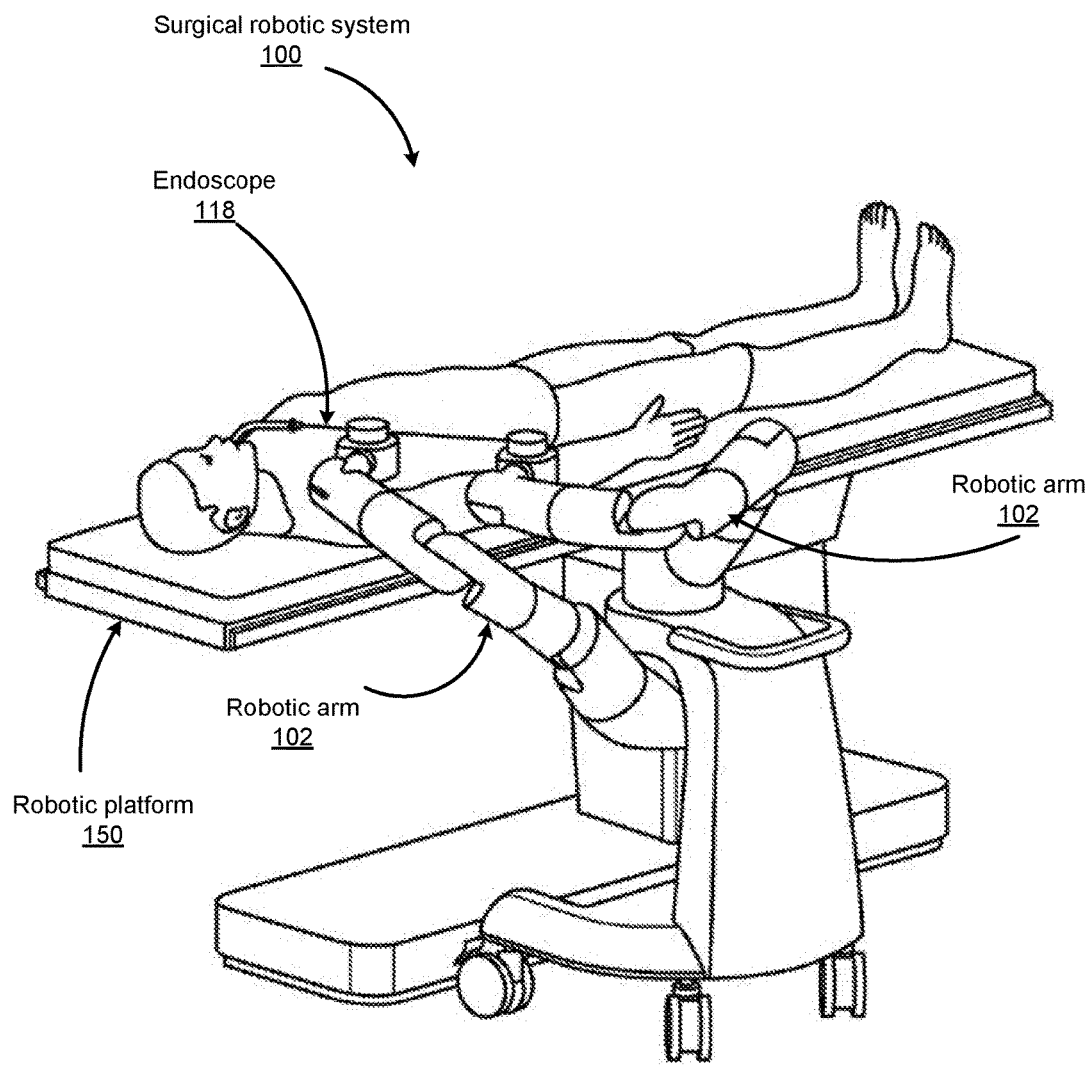
Figure 1E:
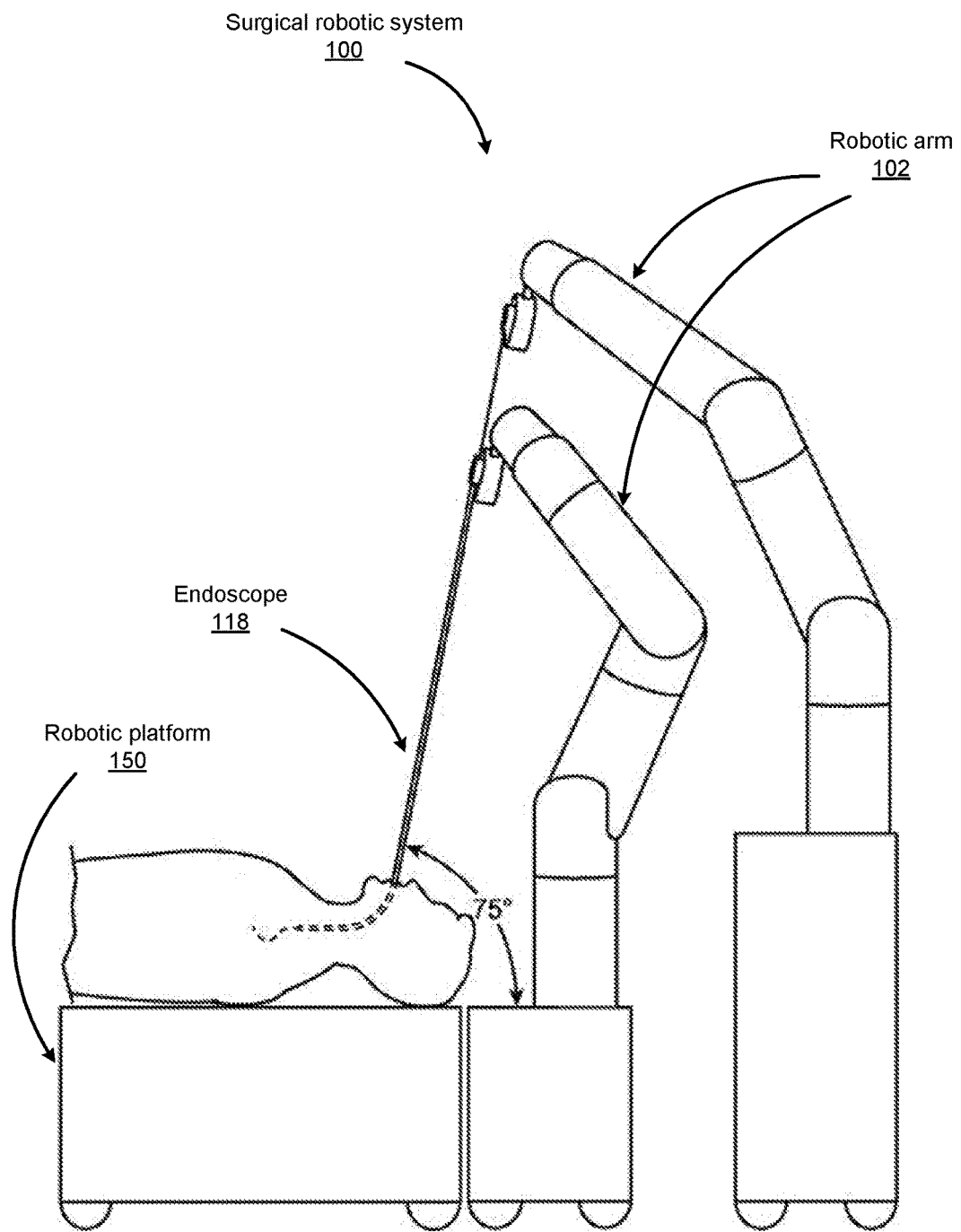
Figure 1F:
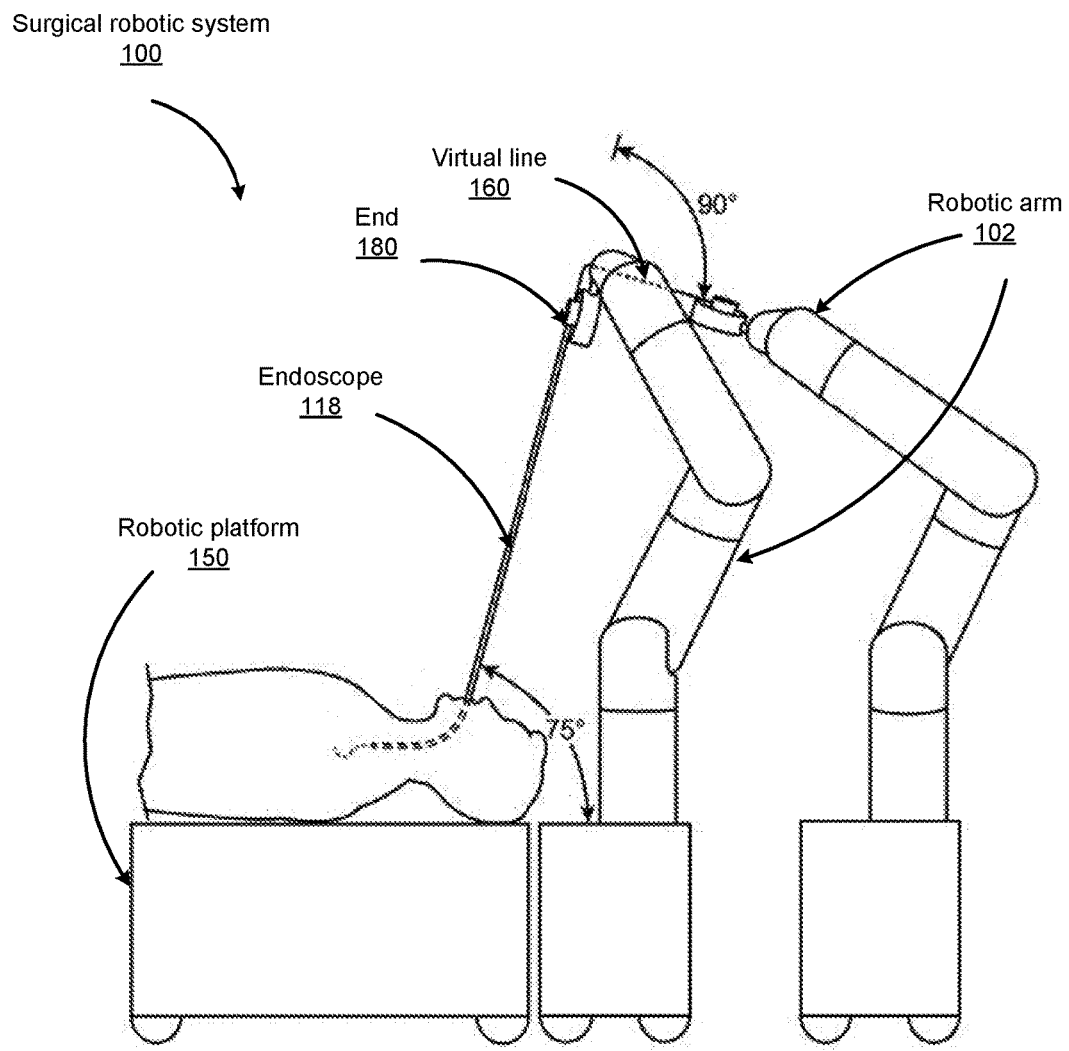

FIGS. 1B-1F show various perspective views of the surgical robotic system 100 coupled to a robotic platform 150 (or surgical bed), according to various embodiments. Specifically, FIG. 1B shows a side view of the surgical robotic system 100 with the robotic arms 102 manipulating the endoscopic 118 to insert the endoscopic inside a patient's body, and the patient is lying on the robotic platform 150. FIG. 1C shows a top view of the surgical robotic system 100 and the robotic platform 150, and the endoscopic 118 manipulated by the robotic arms is inserted inside the patient's body. FIG. 1D shows a perspective view of the surgical robotic system 100 and the robotic platform 150, and the endoscopic 118 is controlled to be positioned horizontally parallel with the robotic platform. FIG. 1E shows another perspective view of the surgical robotic system 100 and the robotic platform 150, and the endoscopic 118 is controlled to be positioned relatively perpendicular to the robotic platform. In more detail, in FIG. 1E, the angle between the horizontal surface of the robotic platform 150 and the endoscopic 118 is 75 degree. FIG. 1F shows the perspective view of the surgical robotic system 100 and the robotic platform 150 shown in FIG. 1E, and in more detail, the angle between the endoscopic 118 and the virtual line 160 connecting one end 180 of the endoscopic and the robotic arm 102 that is positioned relatively farther away from the robotic platform is 90 degree.

I.B Command Console

Figure 2:
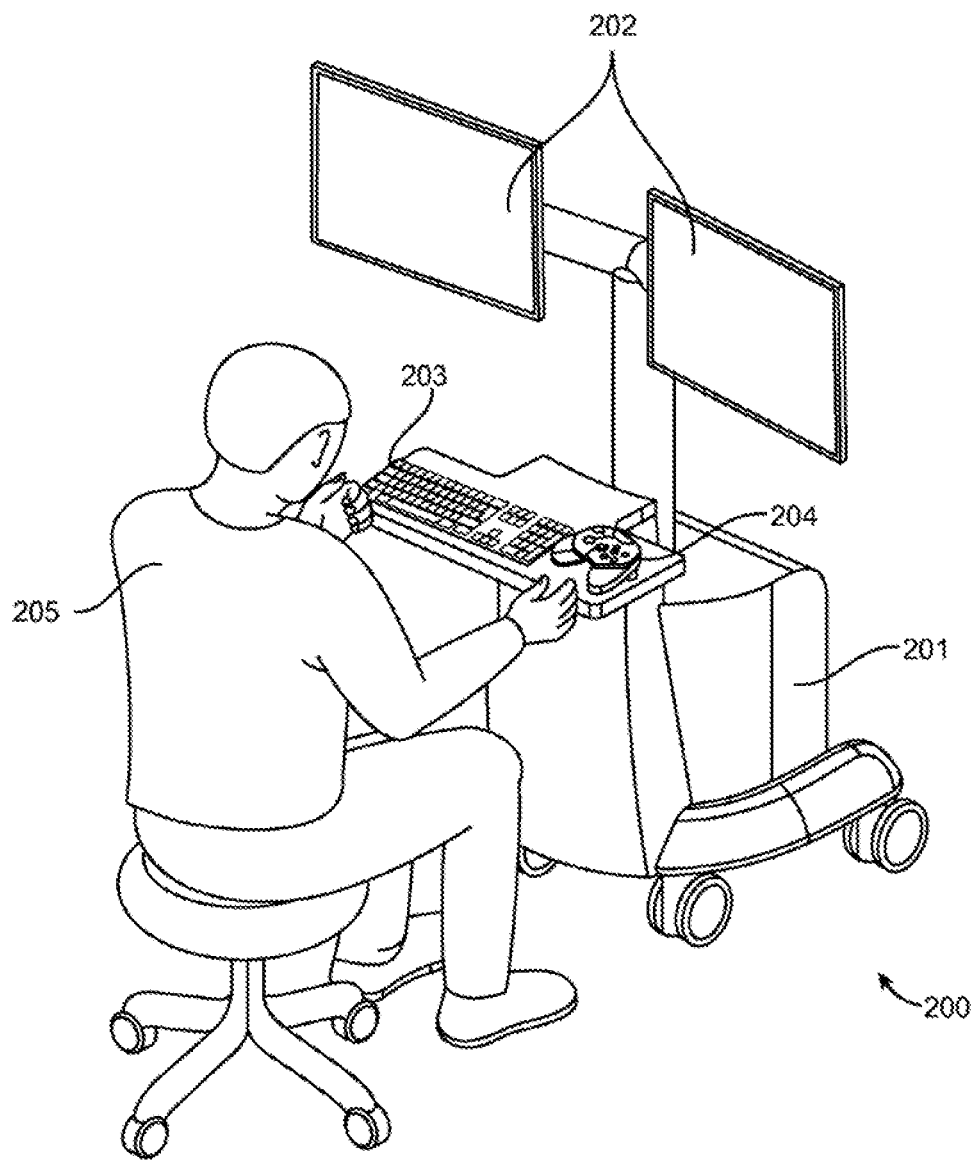
FIG. 2 illustrates a command console for a surgical robotic system according to one embodiment.

FIG. 2 illustrates a command console 200 for a surgical robotic system 100 according to one embodiment. The command console 200 includes a console base 201, display modules 202, e.g., monitors, and control modules, e.g., a keyboard 203 and joystick 204. In some embodiments, one or more of the command module 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay pre-determined optimal navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

I.C. Endoscope

Figure 3A:
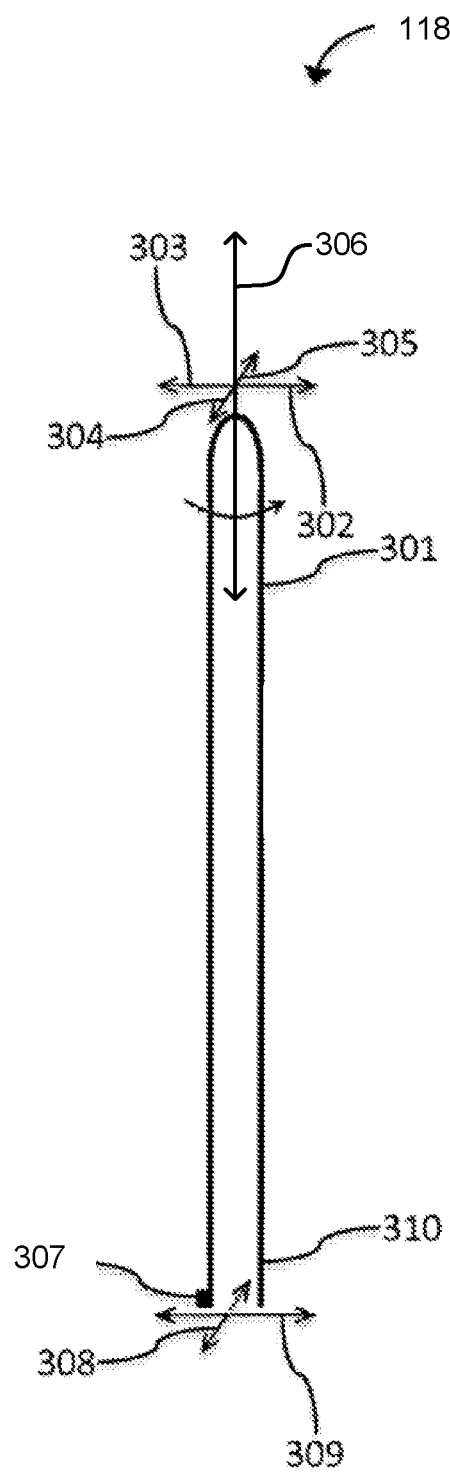
FIG. 3A illustrates multiple degrees of motion of an endoscope according to one embodiment.

FIG. 3A illustrates multiple degrees of motion of an endoscope 118 according to one embodiment. The endoscope 118 is an embodiment of the endoscope 118 shown in FIG. 1. As shown in FIG. 3A, the tip 301 of the endoscope 118 is oriented with zero deflection relative to a longitudinal axis 306 (also referred to as a roll axis 306). To capture images at different orientations of the tip 301, a surgical robotic system 100 deflects the tip 301 on a positive yaw axis 302, negative yaw axis 303, positive pitch axis 304, negative pitch axis 305, or roll axis 306. The tip 301 or body 310 of the endoscope 118 may be elongated or translated in the longitudinal axis 306, x-axis 308, or y-axis 309.

The endoscope 118 includes a reference structure 307 to calibrate the position of the endoscope 118. For example, the surgical robotic system 100 measures deflection of the endoscope 118 relative to the reference structure 307. The reference structure 307 is located on a proximal end of the endoscope 118 and may include a key, slot, or flange. The reference structure 307 is coupled to a first drive mechanism for calculating movement and is coupled to a second drive mechanism, e.g., the IDM 117, to perform a surgical procedure.

Figure 3B:
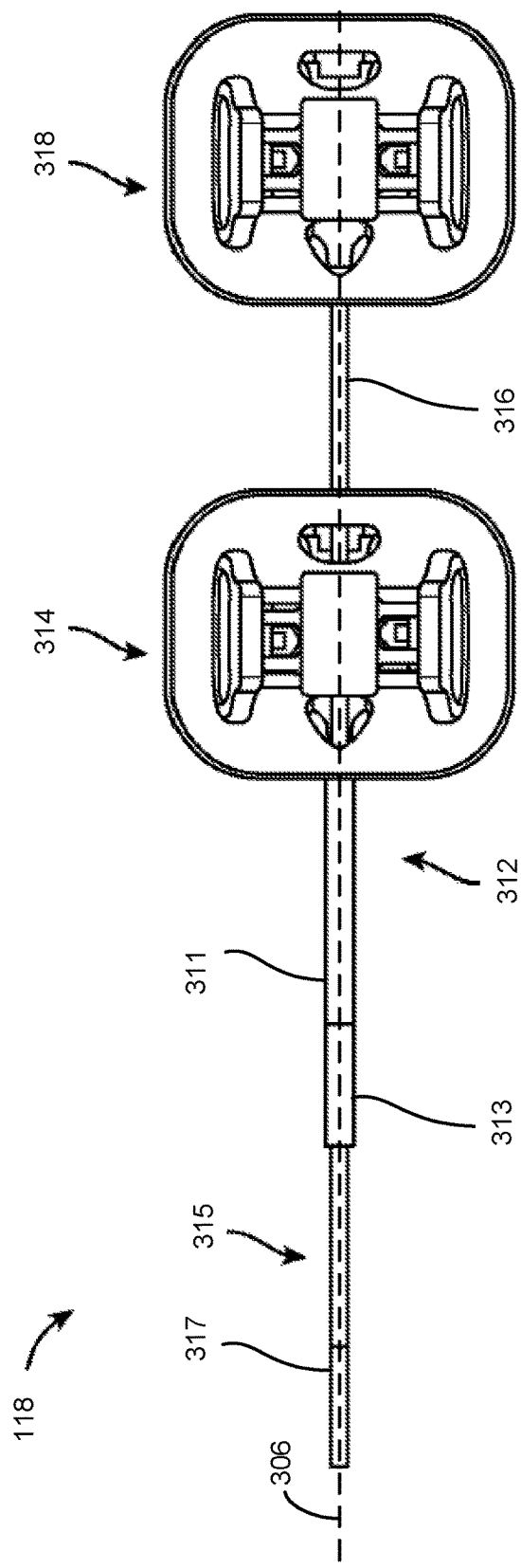
FIG. 3B is a top view of an endoscope according to one embodiment.

FIG. 3B is a top view of an endoscope 118 according to one embodiment. The endoscope 118 includes a leader 315 tubular component nested or partially nested inside and longitudinally-aligned with a sheath 311 tubular component, such that the leader telescopes out of the sheath. The sheath 311 includes a proximal sheath section 312 and distal sheath section 313. The leader 315 has a smaller outer diameter than the sheath 311 and includes a proximal leader section 316 and distal leader section 317. The sheath base 314 and the leader base 318 actuate the distal sheath section 313 and the distal leader section 317, respectively, for example, based on control signals from a user of a surgical robotic system 100. The sheath base 314 and the leader base 318 are, e.g., part of the IDM 117 shown in FIG. 1.

Both the sheath base 314 and the leader base 318 include drive mechanisms (e.g., the independent drive mechanism further described with reference to FIG. 4A-D in Section II.C.4. Instrument Device Manipulator) to control pull wires coupled to the sheath 311 and leader 315. For example, the sheath base 314 generates tensile loads on pull wires coupled to the sheath 311 to deflect the distal sheath section 313. Similarly, the leader base 318 generates tensile loads on pull wires coupled to the leader 315 to deflect the distal leader section 317. Both the sheath base 314 and leader base 318 may also include couplings for the routing of pneumatic pressure, electrical power, electrical signals, or optical signals from IDMs to the sheath 311 and leader 314, respectively. A pull wire may include a steel coil pipe along the length of the pull wire within the sheath 311 or the leader 315, which transfers axial compression back to the origin of the load, e.g., the sheath base 314 or the leader base 318, respectively.

The endoscope 118 can navigate the anatomy of a patient with ease due to the multiple degrees of freedom provided by pull wires coupled to the sheath 311 and the leader 315. For example, four or more pull wires may be used in either the sheath 311 and/or the leader 315, providing eight or more degrees of freedom. In other embodiments, up to three pull wires may be used, providing up to six degrees of freedom. The sheath 311 and leader 315 may be rotated up to 360 degrees along a longitudinal axis 306, providing more degrees of motion. The combination of rotational angles and multiple degrees of freedom provides a user of the surgical robotic system 100 with a user friendly and instinctive control of the endoscope 118.

Figure 3C:
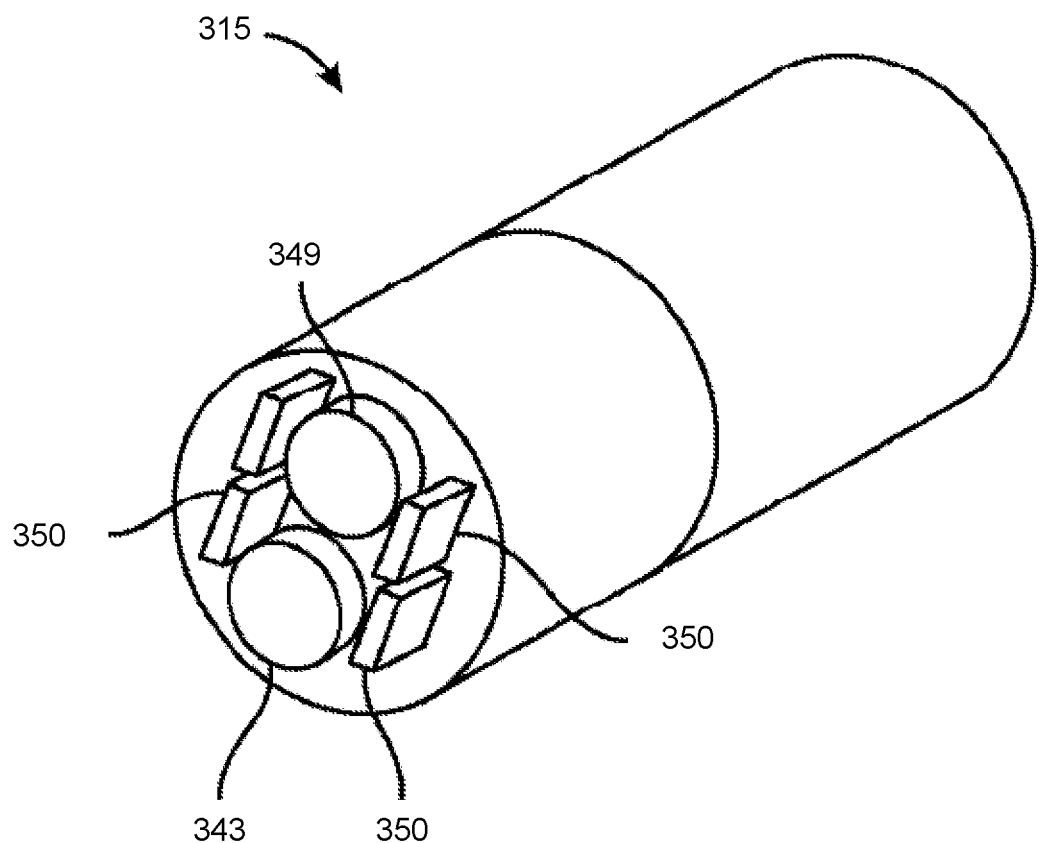
FIG. 3C is a cross sectional isometric view of the leader of the endoscope according to one embodiment.

FIG. 3C is a cross sectional isometric view of the leader 315 of the endoscope 118 according to one embodiment. The leader 315 includes an imaging device 349 (e.g., image sensor, still or video camera, 2D or 3D detector array, charge-coupled device (CCD) or complementary metal-oxide semiconductor (CMOS) camera, imaging fiber bundle, etc.), light sources 350 (e.g., white light source, laser diode, light-emitting diode (LED), optic fiber illuminator, etc.), and at least one working channel 343 for other components. For example, other components include camera wires, an insufflation device, a suction device, electrical wires, fiber optics, an ultrasound transducer, position sensing components, electromagnetic (EM) sensing components, and optical coherence tomography (OCT) sensing components. In some embodiments, the leader 315 includes a pocket hole to accommodate insertion of a component into a working channel 343.

I.C.1. Instrument Device Manipulator

Figure 4A:
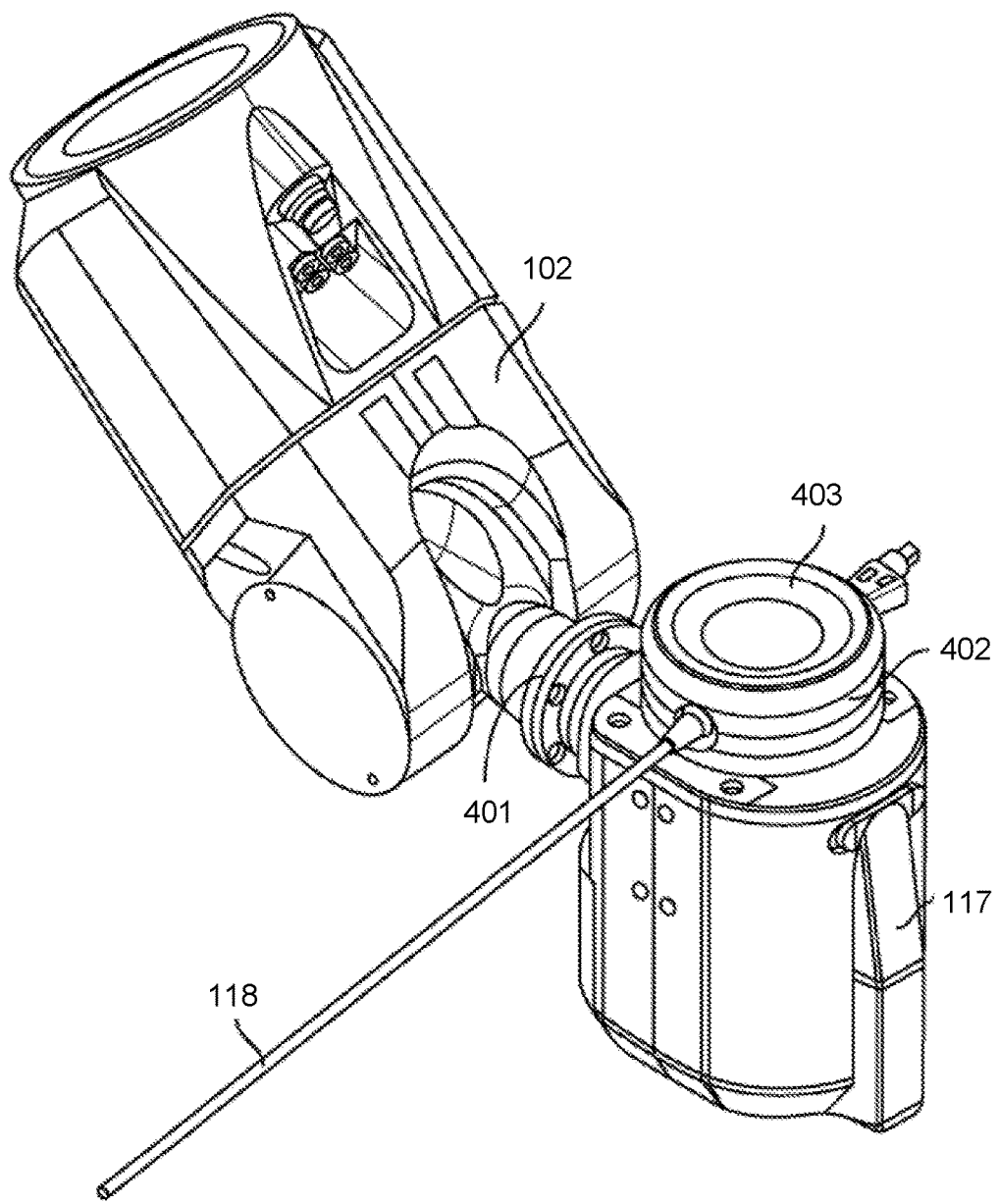
FIG. 4A is an isometric view of an instrument device manipulator of a surgical robotic system according to one embodiment.

FIG. 4A is an isometric view of an instrument device manipulator 117 of the surgical robotic system 100 according to one embodiment. The robotic arm 102 is coupled to the IDM 117 via an articulating interface 401. The IDM 117 is coupled to the endoscope 118. The articulating interface 401 may transfer pneumatic pressure, power signals, control signals, and feedback signals to and from the robotic arm 102 and the IDM 117. The IDM 117 may include a gear head, motor, rotary encoder, power circuits, and control circuits. A tool base 403 for receiving control signals from the IDM 117 is coupled to the proximal end of the endoscope 118. Based on the control signals, the IDM 117 manipulates the endoscope 118 by actuating output shafts, which are further described below with reference to FIG. 4B.

Figure 4B:
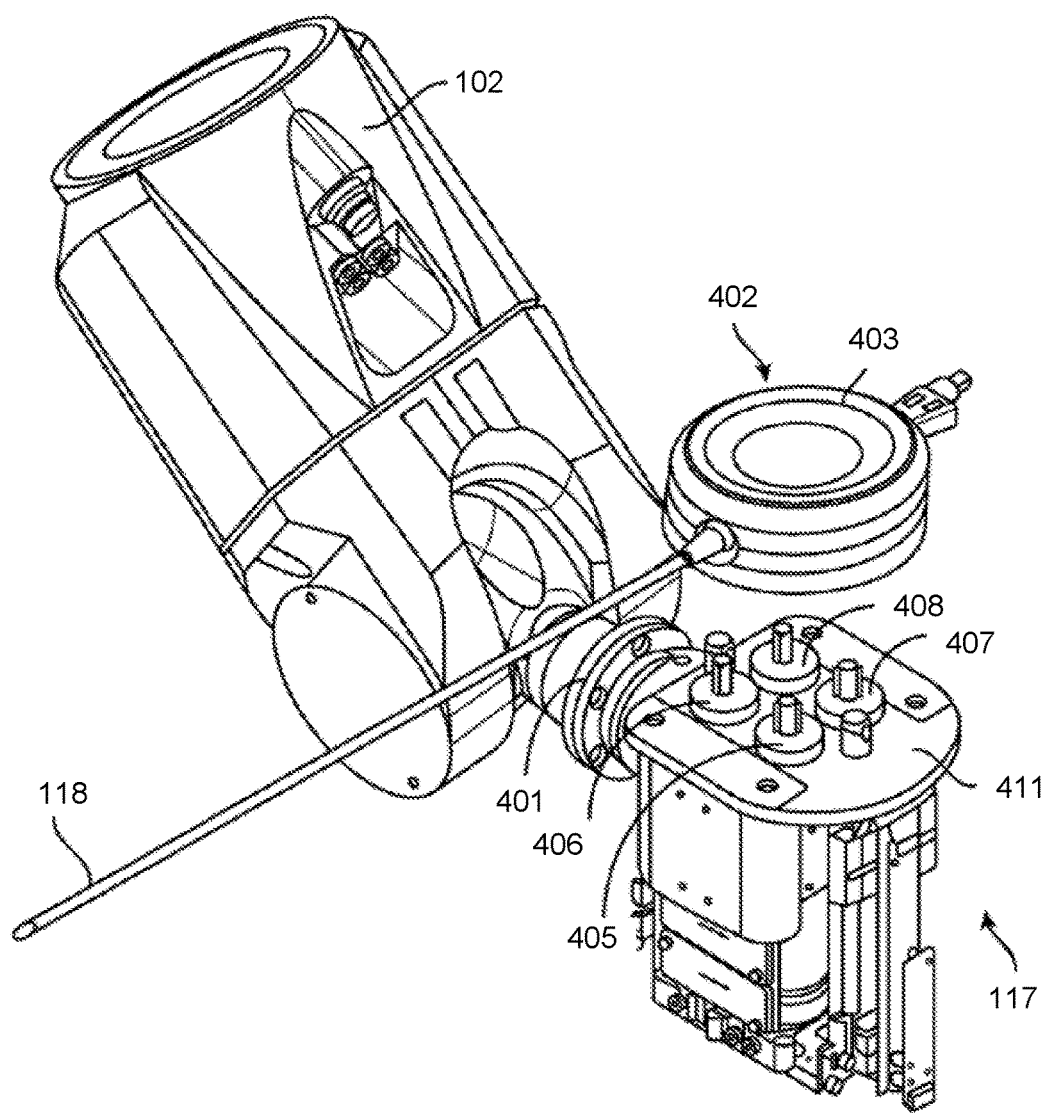
FIG. 4B is an exploded isometric view of the instrument device manipulator shown in FIG. 4A according to one embodiment.

FIG. 4B is an exploded isometric view of the instrument device manipulator shown in FIG. 4A according to one embodiment. In FIG. 4B, the endoscopic 118 has been removed from the IDM 117 to reveal the output shafts 405, 406, 407, and 408.

Figure 4C:
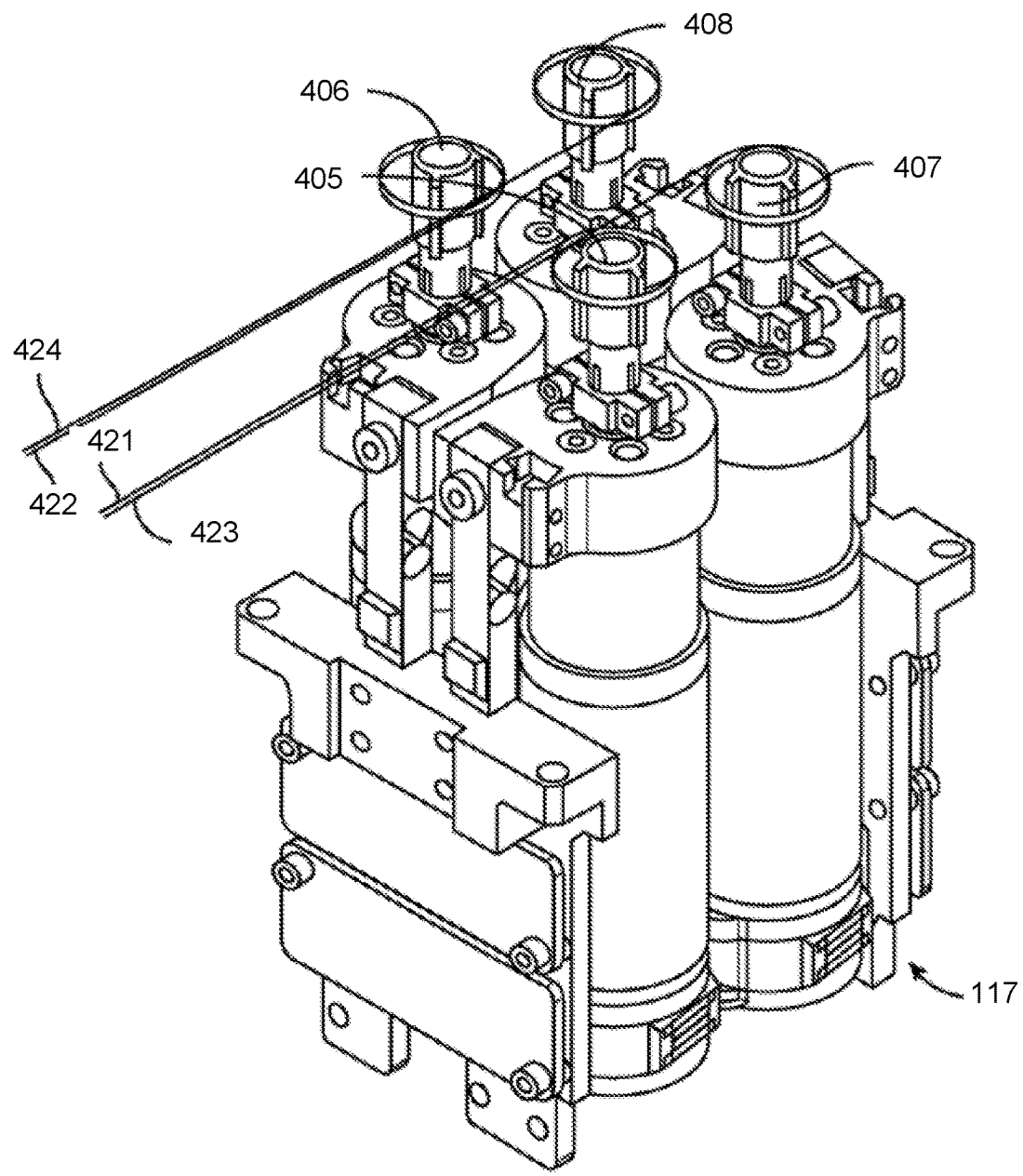
FIG. 4C is an isometric view of an independent drive mechanism of the instrument device manipulator shown in FIG. 4A according to one embodiment.

FIG. 4C is an isometric view of an independent drive mechanism of the instrument device manipulator 117 shown in FIG. 4A according to one embodiment. The independent drive mechanism can tighten or loosen the pull wires 421, 422, 423, and 424 (e.g., independently from each other) of an endoscope by rotating the output shafts 405, 406, 407, and 408 of the IDM 117, respectively. Just as the output shafts 405, 406, 407, and 408 transfer force down pull wires 421, 422, 423, and 424, respectively, through angular motion, the pull wires 421, 422, 423, and 424 transfer force back to the output shafts. The IDM 117 and/or the surgical robotic system 100 can measure the transferred force using a sensor, e.g., a strain gauge further described below.

Figure 4D:
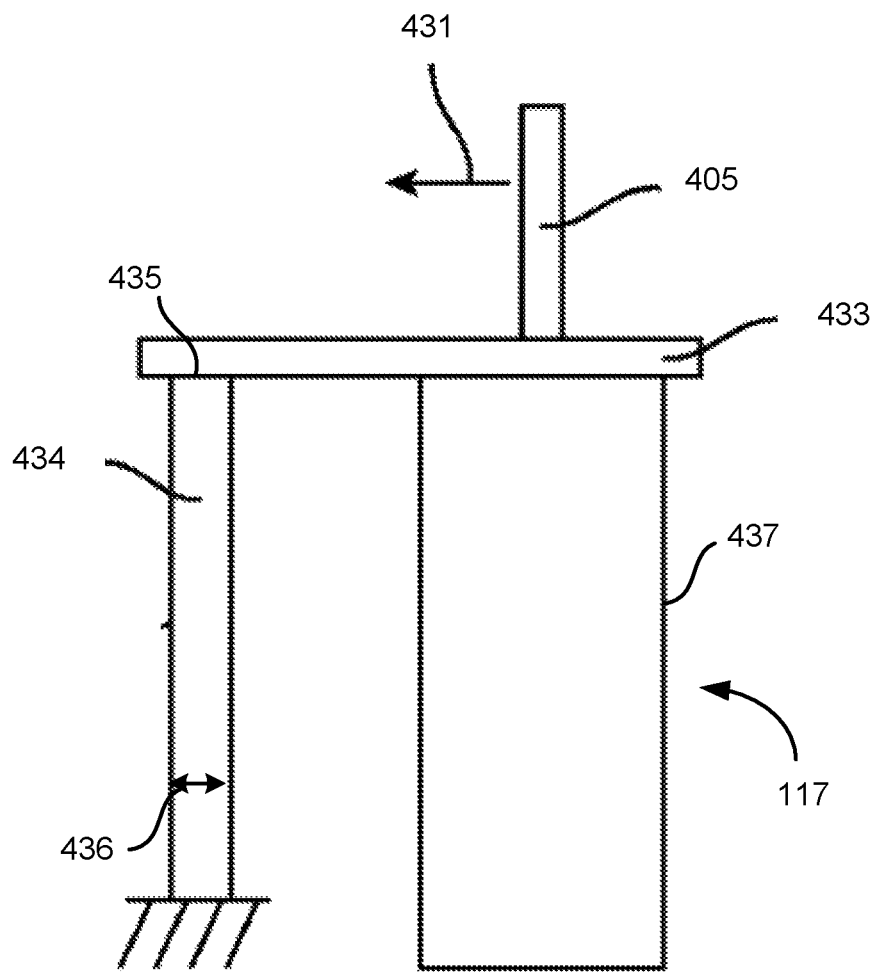
FIG. 4D illustrates a conceptual diagram that shows how forces may be measured by a strain gauge of the independent drive mechanism shown in FIG. 4C according to one embodiment.

FIG. 4D illustrates a conceptual diagram that shows how forces may be measured by a strain gauge 434 of the independent drive mechanism shown in FIG. 4C according to one embodiment. A force 431 may be directed away from the output shaft 405 coupled to the motor mount 433 of the motor 437. Accordingly, the force 431 results in horizontal displacement of the motor mount 433. Further, the strain gauge 434 horizontally coupled to the motor mount 433 experiences strain in the direction of the force 431. The strain may be measured as a ratio of the horizontal displacement of the tip 435 of strain gauge 434 to the overall horizontal width 436 of the strain gauge 434.

In some embodiments, the IDM 117 includes additional sensors, e.g., inclinometers or accelerometers, to determine an orientation of the IDM 117. Based on measurements from the additional sensors and/or the strain gauge 434, the surgical robotic system 100 can calibrate readings from the strain gauge 434 to account for gravitational load effects. For example, if the IDM 117 is oriented on a horizontal side of the IDM 117, the weight of certain components of the IDM 117 may cause a strain on the motor mount 433. Accordingly, without accounting for gravitational load effects, the strain gauge 434 may measure strain that did not result from strain on the output shafts.

I.C.2. Optical Flow

As the endoscope moves, the movement is reflected in changes from one image to the next. These changes may be detected using optical flow techniques that register one image to another, from which a movement may be estimated.

FIG. 5A is a flowchart of a process for determining movements of an endoscope from a sequence of recorded images according to one embodiment. The process 500 may include different or additional steps than those described in conjunction with FIG. 5A in some embodiments, or perform steps in different orders than the order described in conjunction with FIG. 5A.

The image registration module 130 of the surgical robotic system 100 shown in FIG. 1 determines movement of an endoscope tip based on changes in properties of a sample of images (e.g., grayscale or color) captured by an image sensor coupled to the endoscope tip, e.g., the imaging device 349 of endoscope 118 shown in FIG. 3C. Because the image sensor is coupled to the endoscope 118, the image registration module 130 assumes that changes between a pair of images of the sample are due to a shift in perspective of the image sensor corresponding to a movement of the endoscope tip, e.g., translation, rotation, and/or scaling in a pitch or yaw axis.

The image registration module 130 can filter the sample of images, for example, by removing every other image of the sample to help reduce the time required to process the sample. In some embodiments, the image registration module 130 extracts the sample of images from a video captured by the image sensor. Image registration does not require the source and target images to be subsequent frames of the camera. However, the accuracy of the motion estimated by image registration tends to be greater as the time period between images decreases. Thus, the image registration module 130 generates more accurate motion estimates (e.g., nearly continuous measurement of parameters associated with movement of the endoscope) by registering many images in sequence.

To determine translation movement, the image registration module 130 receives 510 a sample of images and analyzes pairs of images of the sample using an optical flow technique. In a pair of images, the image that occurs first is referred to as the source image and the image that occurs second is referred to as the target image. The order of the first and second images is arbitrary. Thus, the direction of translation (e.g., moving forward or backward in time) is determined based on which image is considered the source and which images is considered the target. In one embodiment, each image is a two-dimensional pixel array of N pixel values corresponding to light intensities (e.g., for grayscale images), vectors representing intensities of different colors of light (e.g., for color images), etc. The image registration module 130 can transform the two-dimensional pixel array into a corresponding 1-dimensional array with N elements for processing.

The image registration module 130 generates 520 a difference array D and generates 530 a gradient array G based on the pair of images. In some embodiments, the image registration module 130 generates a difference array and gradient array for each pair of images of the sample. The difference array D is based on the difference between a pixel value of the target image and a corresponding pixel value of the source image. The gradient array G is based on a weighted average of the rate of change (e.g., derivative) of a pixel value of the target image and the rate of change of a corresponding pixel value of the source image. In embodiments with a two-dimensional (e.g., x and y dimensions) pixel array, the rate of change of a pixel in the x-dimension $G_x$ is based on the difference between the pixel and each of two or more adjacent pixels in the x-direction. Similarly, the rate of change of the pixel in the y-dimension $G_y$ is based on the difference between the pixel and each of two or more adjacent pixels in the y-direction. The gradient array may be a weighted average of the rates of change in the x and y dimensions, e.g., equally weighted. The image registration module 130 can decompose the 2D gradient array into two sub-arrays, $G_x$ and $G_y$, corresponding to partial derivatives in the x and y directions, respectively. Accordingly, the image registration module 130 represents G as an N×2 matrix: $G=(G_x\ G_y)$, where $G_x$ and $G_y$ each include N components.

The image registration module 130 determines a motion of the endoscope base on the difference array D and the gradient array G. The motion can be represented by a vector p. The vector p often comprises a set of model parameters, and the identities of these parameters may be varied in order to detect different properties of motion. In general, p may be modeled as satisfying a linear equation of the form $Ap=v$, wherein A is a matrix determined by G and the form of p, and v is a vector corresponding to D. The value of p in the above equation may be solved by methods such as least-squares fitting, in which p may be estimated as $p=(A^TA)^{-1}A^Tv$, where $A^T$ represents the transpose of A and $(A^TA)^{-1}$ represents the inverse of the product of $A^T$ with A. The solved p represents a motion (e.g., translation, rotation) of the endoscope. The image registration module 130 can repeat the steps 520-540 of the process 500 for multiple pairs of images of the sample. Thus, the image registration module 130 generates a set of motion vectors corresponding to each processed pair of images.

I.C.3. EM Registration

Figure 5B:
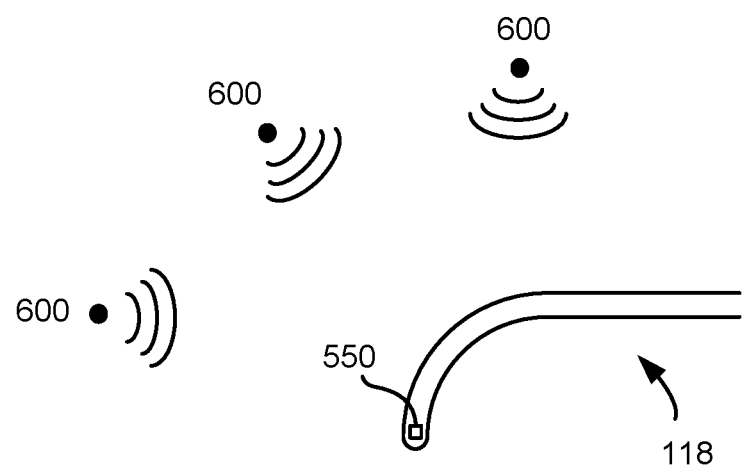
FIG. 5B is a diagram of electromagnetic tracking system according to one embodiment.

FIG. 5B is a diagram of electromagnetic tracking system according to one embodiment. The spatial sensor 550 coupled to the tip of the endoscope 118 is an EM sensor 550 that detects an electromagnetic field (EMF) generated by one or more EMF generators 600 in proximity to the endoscope 118. The strength of the detected EMF is a function of the position and/or orientation of the endoscope 118. In one embodiment, a number of EMF generators 600 are located externally to a patient. The EMF generators 600 emit EM fields that are picked up by the EM sensor 550. The different EMF generators 600 may be modulated in a number of different ways so that when their emitted fields are captured by the EM sensor 550 and are processed by the controller 120 (or any computer system external to the surgical robotic system 100), their signals are separable. Further, the EMF generators 600 may be oriented relative to each other in Cartesian space at non-zero, non-orthogonal angles so that changes in orientation of the EM sensor 550 will result in the EM sensor 550 receiving at least some signal from at least one of the EMF generators 600 at any instant in time.

The controller 120 registers EM data captured by the EM sensor 550 to an image of the patient captured with a different technique other than EM (or whatever mechanism is used to capture the alignment sensor's data), such as a computed tomography (CT) scan, to establish a reference frame for the EM data. In some embodiments, the distal end of the endoscope may be tracked by EM sensors located in the tip. The relative location within the patient may be determined by comparing a pre-operative model generated from CT data to the absolute location measured by the EM tracking system.

For example, before registering EM data with a 3D model generated from the CT data, data points derived from the EM data are initially located far from the position of the endoscope tip moving along a planned navigation path expected from the 3D model. This position difference between the EM data and the 3D model reflects the lack of registration between the EM coordinates and the 3D model coordinates. The controller 120 may determine and adjust the points on the 3D model based on correlation between the 3D model itself, image data received from the imaging device (e.g., cameras) on the tip and robot data from robot commands (e.g., provided to the robotic arms of the surgical robotic system 100). The controller 120 uses the 3D transformation between these points and collected EM data points to determine the initial registration of the EM coordinate system to the 3D model coordinate system. After registering EM data with the 3D model, the data points derived from EM data fall along the planned navigation path derived from the 3D model, and each data point among the data points reflects a measurement of the position of endoscope tip in the coordinate system of the 3D model.

I.C.4 Endoscope Procedure

Figure 6A:
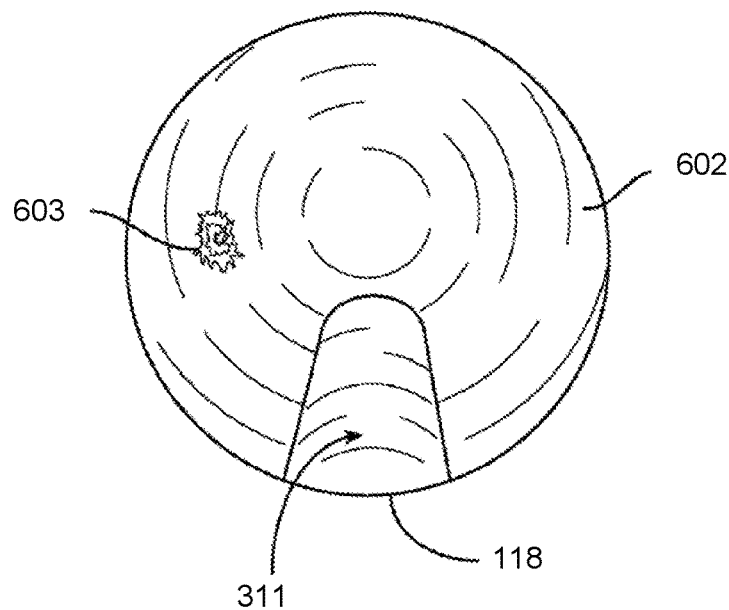
FIG. 6A illustrates the distal end of an endoscope within an anatomical lumen according to one embodiment.
Figure 6B:
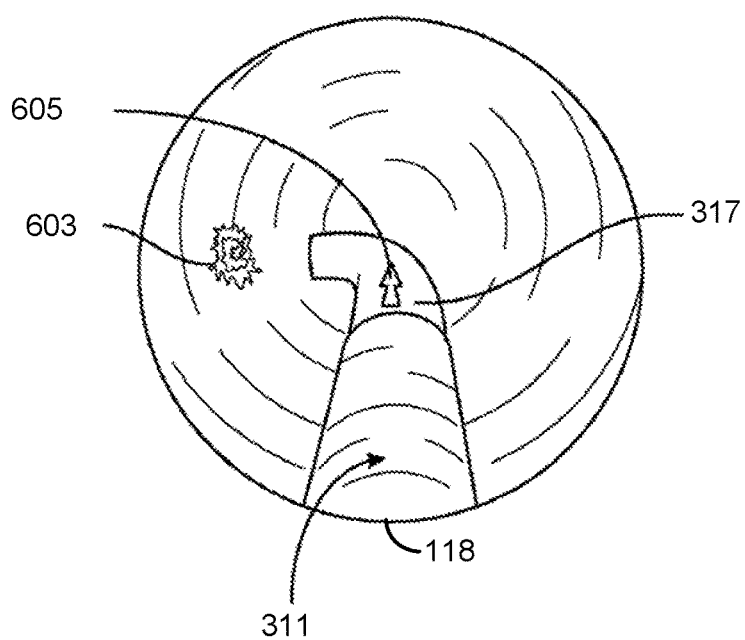
FIG. 6B illustrates the endoscope shown in FIG. 6A in use at an operative site according to one embodiment.
Figure 6C:
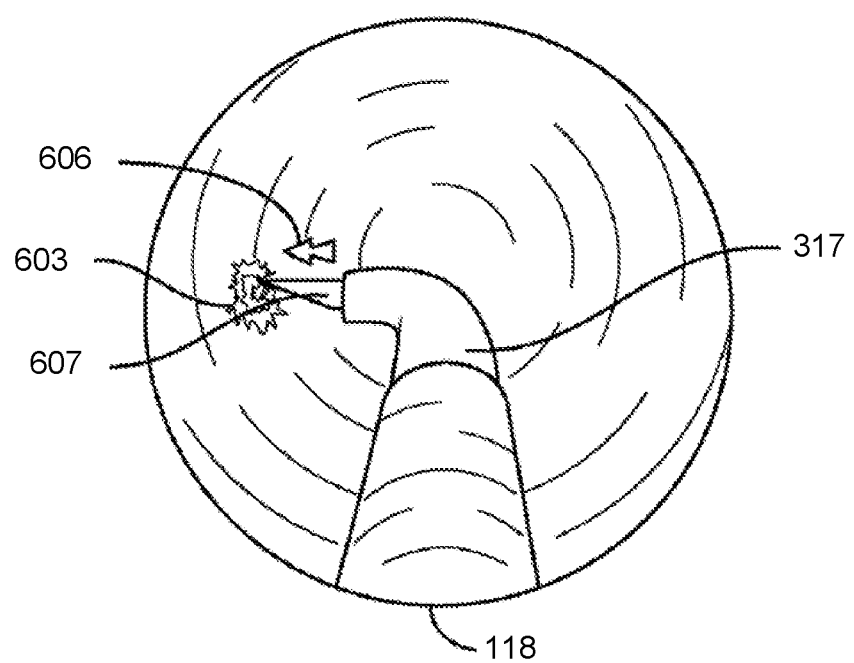
FIG. 6C illustrates the endoscope shown in FIG. 6B with an aspiration needle according to one embodiment.

FIGS. 6A-C illustrate example surgical procedures using an endoscope, e.g., endoscope 118 shown in FIG. 3A. FIG. 6A illustrates the distal end of the endoscope 118 within an anatomical lumen 602 according to one embodiment. The endoscope 118 includes a sheath 311 and navigates through the anatomical lumen 602 inside a patient toward an operative site 603 for a surgical procedure.

FIG. 6B illustrates the endoscope 118 shown in FIG. 6A in use at the operative site 603 according to one embodiment. After reaching the operative site 603, the endoscope 118 extends a distal leader section 317, longitudinally aligned with the sheath 311, in the direction marked by arrow 605. The endoscope can also articulate the distal leader section 317 to direct surgical tools toward the operative site 603.

FIG. 6C illustrates the endoscope 118 shown in FIG. 6B with an aspiration needle 1007 according to one embodiment. In cases where the operative site 603 includes a lesion for biopsy, the distal leader section 317 articulates in the direction marked by arrow 606 to convey the aspiration needle 1007 to target the lesion.

In some embodiments, the distal leader section 317 is integrated with the sheath 311 (not shown in FIG. 6). The distal leader section 317 navigates with the sheath 311 through the anatomical lumen 602 inside a patient toward an operative site 603 for a surgical procedure. After reaching the operative site 603, surgical tools can be directed to the operative site 603 via the distal leader section 317.

In some embodiments, the distal leader section 317 can be deployed through a working channel that is off-axis (neutral axis) of the sheath 311, which allows the distal leader section 317 to operate without obscuring an image sensor (not shown in FIG. 6) coupled to the end of the sheath 311 (or any other location of the endoscope 118). This arrangement allows the image sensor to capture images inside the anatomical lumen while the endoscope 118 articulates the distal leader section 317 and keeps the sheath 311 stationary.

The construction, composition, capabilities, and use of distal leader section 317, which may also be referred to as a flexure section, are disclosed in U.S. patent application Ser. No. 14/201,610, filed Mar. 7, 2014, and U.S. patent application Ser. No. 14/479,095, filed Sep. 5, 2014, the entire contents of which are incorporated by reference.

II. Endolumenal Buckling Detection

As introduced above, endolumenal buckling is a phenomenon whereby a flexible instrument (e.g., endoscope) navigated within anatomical lumens towards an operative site or a surgical site prolapses in an undesired direction within the anatomical lumen in response to an insertion force.

Figure 7A:
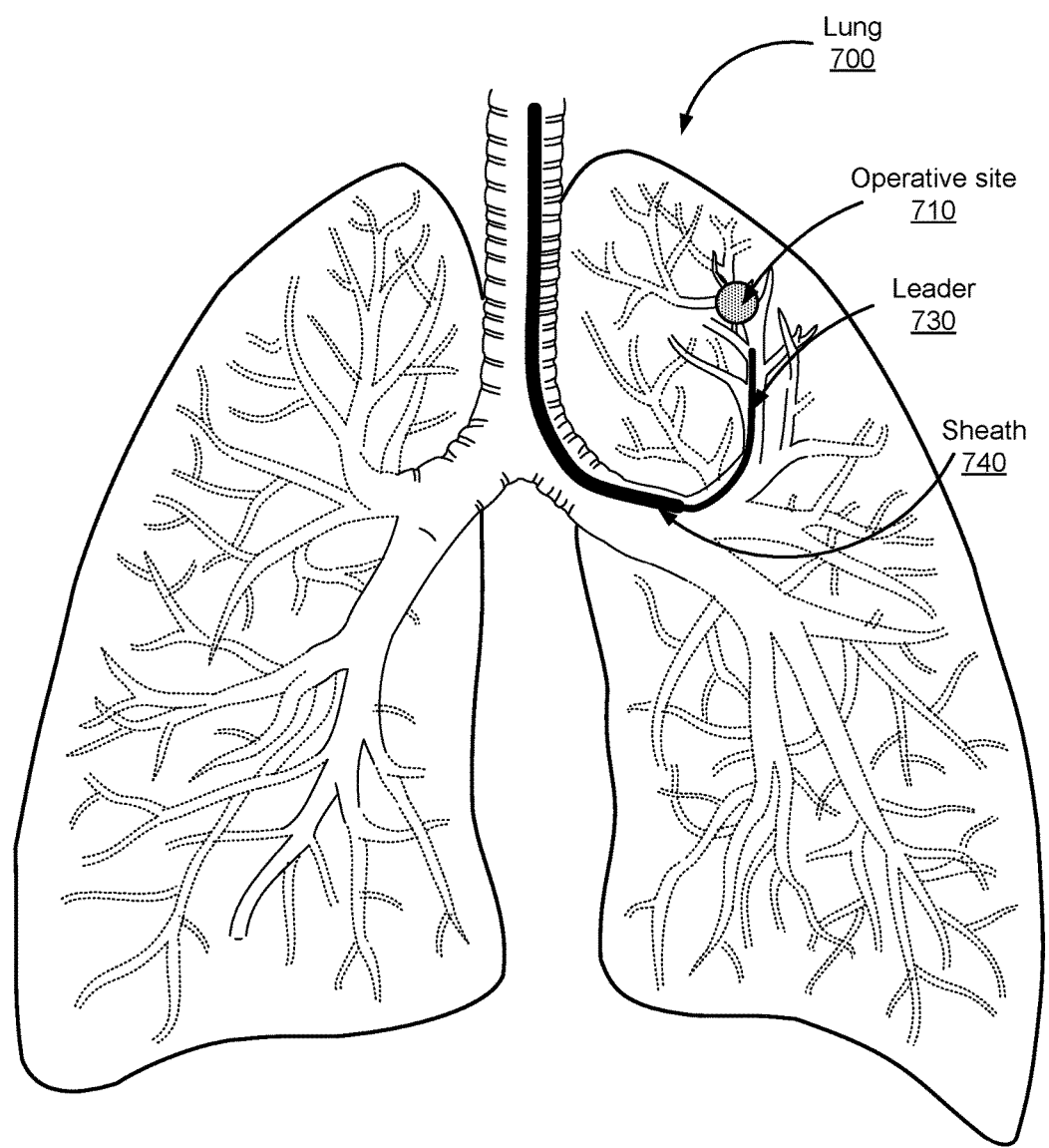
FIGS. 7A, and 7B illustrate an example of endolumenal buckling occurred when an endoscope is inserted into a patient's lung to an operative site according to one embodiment.
Figure 7B:
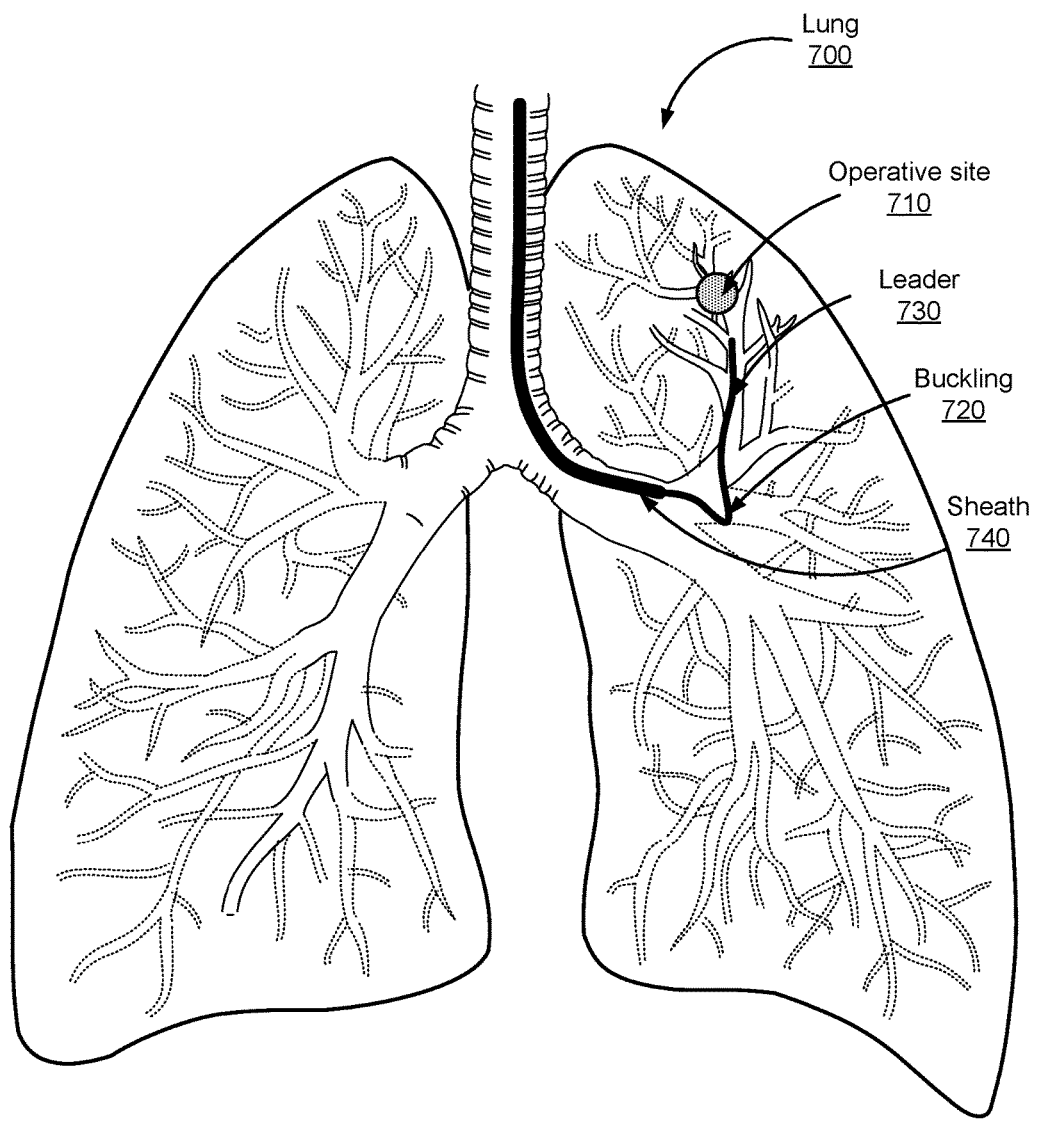

FIGS. 7A and 7B illustrate an example of endolumenal buckling occurring when an endoscope is inserted into a patient's lung 700 to an operative site 710. The endoscope 118 is inserted into a patient's mouth, down the patient's trachea, and into the patient's lung 700. As shown in FIG. 7A, the endoscope bends normally towards the operative site 710 located in a left upper lobe of the lung 700. The sheath 740 of the endoscope is navigated to the left main bronchus first, and then the leader 730 is navigating in tertiary bronchi towards the operative site 710. As shown in FIG. 7B, as the leader 730 is navigating towards the operative site 710, a distal leader section of the leader 730 gets stuck or blocked and therefore does not move forward. As more insertion force is applied, a portion of the endoscope buckles 720 rather than to forcing the leader further.

Improper placement of the sheath 740 relative to the operative site 710 may also result in undesirable buckling of the endoscope. For example, if the sheath 740 is inserted and advanced only to the trachea, the leader 730 will not be supported when attempting to insert into the upper lobe of patient's lung 700 in order to reach the operative site 710. In this example, the insertion force on the sheath 740 is directed "downward", i.e., towards the lower lobes of the patient's lung 700, in the opposite direction of the upper lobes, where the operative site 710 is located. In contrast, when the sheath 740 is positioned deeper into the lung, i.e, closer to the operative site, so the sheath 740 is directed in a more "upward" position, or at least a more "neutral" position, the insertion force vector on the leader 730 is may be more aligned with the direction of the operative site 710. In the latter example, greater insertion may be achieved with lower amounts of insertion force applied to the sheath 740, in addition to a reduction in prolapsing or buckling by the leader 730.

II.A. Detecting Endolumenal Buckling within a Patient Lumen

Endolumenal buckling may occur in a variety of ways. For example, the tip of the leader of the endoscope may become stuck or nearly stuck, and a portion of the leader or sheath may bends with a great amount of curvature as the endoscope is further inserted into the patient. The bucked portion stores potential energy and generates an opposing force that attempts to push the endoscope backward.

Accordingly, there are a number of regions of interest where it may be advantageous to place sensors to detect buckling. As an example, three main regions of arbitrary "size" can be defined. A first region may cover the volume near the tip of the leader. A second region covers a portion of the leader in a range from an end of the sheath within the patient to the edge of the first region. A third region may cover the end of the sheath where the leader extends from as well as the portion of the sheath proximal to its end (also referred to as the distal sheath section).

For each sensor region, one or more sensors can be placed in any one of several locations. Examples of sensor locations include outer surface of the sheath or the leader, walls of the sheath or the leader, inner surface of sheath's lumen, inner surface of conduits of the leader or the sheath, one or more locations on pull wires of the leader or the sheath, another suitable location within the sensor region to place sensors, or some combination thereof.

FIGS. 8A-B illustrate examples of sensor regions used to place sensors according to one embodiment. FIG. 8A shows the leader 730 bends normally towards the operative site 710 at time T=$T_1$ 860A, and FIG. 8B shows the leader 730 buckles when the leader 730 is inserted more at time T=$T_2$ 860B. $T_1$ 860A and $T_2$ 860B are consecutive, or are separated with a time interval. As shown in FIGS. 8A and 8B, a region of interest (ROI) 810 is selected and zoomed in. The ROI 810 includes the leader 730 and a portion of the sheath 740. The zoomed-in ROIs without lung structures are shown at bottom of FIG. 8A and FIG. 8B, respectively. Sensor region A 820 includes the tip of the leader 730 and a small portion proximal to the tip. The sensor region B 830 covers a portion of the leader 730 in the range from the end of the sheath 740 within the patient to the tip of the leader 730. The sensor region C 840 includes the end of the sheath and a small portion of the distal sheath section.

One or more different types of sensors can be placed in each sensor region. For example, one or more position sensors, one or more force sensors, one or more shape sensors or some combination thereof can be placed in each sensor region. Examples of types of sensors include a position sensor (e.g., EM sensor, optical sensor, accelerometer, gyroscope, magnetometer, another suitable type of sensor that detects motion, or some combination thereof), a force sensor (e.g., resistance sensor, pressure sensor, strain gauge, torque sensor, friction sensor, another suitable type of sensor that detects various types of forces, or some combination thereof), an image sensor (e.g., CCD, CMOS, NMOS, another suitable type of sensor that detects and conveys the information that constitutes an image, or some combination thereof), a shape sensor (e.g., optical fiber shape sensor, another suitable type of sensor that detects boundary, outline or surface of an object, or some combination thereof).

Sensor data captured from one or more sensor regions can be compared with expected data (also referred to as historical data or reference data) to determine if buckling has occurred. The expected data describes data associated with various characteristics caused by a motion of the endoscope during a navigation. Examples of the expected data include data associated with various expected statuses caused by the motion of the endoscope, sensor data captured from one or more different sensor regions, different types of sensor data captured from the same sensor region, different types of sensor data captured from one or more different sensor regions, or some combination thereof. More specifically, expected data includes data associated with various possible states/statuses caused by the motion of the endoscope. Examples of expected statuses include expected position of the tip or distal end of the sheath, expected position of a portion of the leader or sheath, expected bending shape of the leader or sheath, expected force generated by the expected bending of the leader or sheath, expected force detected by the tip of the leader or sheath, or any other measurable or derivable quantity relating to the state of the endoscope which may include, but is not limited to, shape, distance, length, slope, gradient, curvature, angle, etc., or some combination thereof.

The sensor data (also referred to measured data) collected from the sensors in the instrument during operation indicates a measured status based on an actual motion of the corresponding sensor regions where those sensors are placed. Examples of the measured statuses include a similar list of statuses as the list of expected statuses provided in the immediately previous paragraph. For example, sensor data collected from an imaging device on the tip (also referred to as optical flow data), or sensor data collected from an EM sensor located on the tip both can indicates a measured state (e.g., a position of the tip). In some embodiments, by comparing "endo view" with the sensor data, the surgical robotic system 100 determines a measured status indicating a relative location of the tip within the patient. When the measured status indicated by the sensor data does not match or correlate to the expected status indicated by the expected data, the surgical robotics system 100 determines that endolumenal buckling has occurred. Examples are further described in Section II.A.1.

Sensor data captured from one or more sensor regions can be compared with sensor data from the same and/or different sensor regions to determine if endolumenal buckling has occurred. For example, if sensor data captured from the one or more sensor regions indicates that the corresponding sensor regions of the endoscope have undergone a first status change (e.g., a status change indicating a force change in the first region), and sensor data from a different sensor region, or a different type of sensor data from the same sensor region indicates that the corresponding sensor region or sensor types has undergone a second status change (e.g., a status change indicating a force change in the third region, or a status change indicating that the tip has not moved in the first region), the surgical robotics system 100 determines that endolumenal buckling has occurred. Examples are further described in Section II.A.2.

Generally, a status change indicates that some quantity measurable or derivable from the sensor data, which may include measured and expected sensor data, has changed one of more or less than a threshold, often measured over some period of time (e.g., $T_1$ and $T_2$). There are a number of different types of status changes.

A first type of status change is a position change of some portion of the endoscope being less than a position threshold, representing a range of motion where the portion of the endoscope has not moved an appreciable distance, generally in response to an endoscope insertion command. A first example of the first type status change is where the tip of the leader or the end of the sheath within the patient has not moved or has moved less than a threshold amount in response to the command. For example, when an endoscope enters into an organ with a complex tubular network (e.g., a tubular network with variable bending, or with variable diameter), a certain insertion force is applied to the endoscope in order to move the endoscope to a target location. If the status change indicates that the tip of the leader or the end of the sheath within the patient has moved less than a threshold amount in response to the command, the surgical robotics system 100 may determine that endolumenal buckling has occurred based or this status change alone, or in combination with other types of status change, as further described in Section II.A.2. A second example is where a portion of the leader or a portion of the sheath does not move to an expected position, in response to the command. A third example is where a portion of the sheath (e.g., the end of sheath, a distal sheath section) has been retracted in response to the command.

A second type of status change is a force change above a threshold in response to a command that is detected at the tip of the leader, a portion of the distal leader section, the end of sheath, a portion of the distal sheath section.

A third type of status change identifies an unwanted motion, generally bending, along the leader or the sheath, generally in response to an endoscope insertion command. One example of the third type status change include a bending change (e.g., a slope change, a gradient change, a curvature change, etc.) among two or more points along the leader or the sheath equals or exceeds a bending threshold, representing a situation where the leader or the sheath has appreciably bent in an unexpected manner in response to the command. Another example of the third type status change include a distance change between two points along the leader or the sheath less than a distance threshold, representing a situation where the distance between the two points has been shortened unexpectedly, in response to the command. Another example of the third type of status change occurs in instances such as when navigating the endoscope through a turn in the patient's endolumenal network is such that bending is expected but where that bending does not occur along the section of the endoscope where it is expected to occur. Thus, a lack of a bending change as measured by sensors along some points of the endoscope may suggest that bending has instead occurred elsewhere along the endoscope.

Although the above description describes the sensors as being associated with regions, this region association does not need to be explicitly made use of in the data processing system that uses the sensor data to determine whether buckling has occurred. In such an implementation, assignment of sensors to regions merely serves as a convenient way for distinguishing different sensors placed within the instrument, and in practice other differentiable characteristics may be used such as position along the sheath or leader, etc.

Figures 9A, 9B:
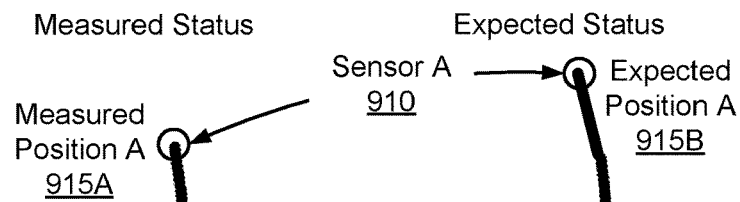

II.A.1. Endolumenal Buckling Detection Based on a Comparison Between Measured Status and Expected Status FIGS. 9A-9L illustrate examples of endolumenal buckling detection based on a comparison between measured status and expected status according to one embodiment. As discussed above, one or more different types of sensors can be placed in the same sensor region to detect endolumenal buckling. As shown in FIGS. 9A-9B, a sensor A, such as position or force sensor, is placed in the first sensor region (e.g., tip of the endoscope). FIGS. 9A-9B show a measured position A 915A and an expected position A 915B indicated by the sensor A 910. For example, in response to an insertion command to move the endoscope to an expected position A 915B, the endoscope is inserted to a measured position A 915A. Compared with the expected position A shown in FIG. 9B, the measured position A shown in FIG. 9A is still or has moved only slightly, thereby indicating that buckling has occurred. Similarly, a measured force in FIG. 9A (e.g., a friction force generated between the tip and the lung structure) may be greater than the expected force in FIG. 9B based on the command input, thereby indicating that buckling has occurred.

Figures 9C, 9D:
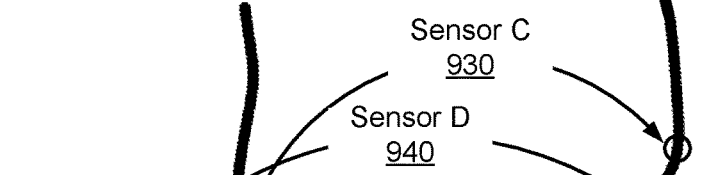

As shown in FIGS. 9C-9D, a sensor C and a sensor D are placed in the second sensor region (e.g., a portion of the leader). In a first embodiment, both sensors C and D are position sensors. In FIG. 9C, in response to a command to move the second region to an expected positions C and D, the sensor C detects a measured position C and the sensor D detects a measured position D. The measured position C and measured position D are compared with the expected position C and the expected position D. The comparison indicates whether the measured positions (based on the raw data or some derivation thereof such as the distance between them) deviate from the expected positions more than a threshold (not matching) or less than a threshold (matching). If measured and expected match, the surgical robotics system determines that buckling has not occurred, and that it has occurred if they do not. Examples of derived parameters used for detecting buckling include a slope, a distance, curvature, a gradient, another suitable parameter derived from the two positions, or some combination thereof.

In a second embodiment, sensors C and D are force sensors. In response to a command to insert the endoscope having an expected forces A and B in the second region, the sensor C detects a measured force A (e.g., a first torque) and the sensor D detects a measured force B (e.g., a first torque) in FIG. 9C. The measured force A and measured force B are compared with the expected force A and the expected force B. The comparison indicates whether the measured forces (based on the raw data or some derivation thereof) deviate from the expected forces more than a threshold (not matching) or less than a threshold (matching). If the measured and the expected match forces, the surgical robotic system 100 determines that buckling has not occurred, and that it has occurred if they do not.

In a third embodiment, the sensor C and the sensor D have different sensor types. For example, the sensor C is a position sensor and the sensor D is a force sensor. In response to a command to insert the endoscope having an expected position C and an expected force B in the second region, the sensor C detects a measured position C and the sensor D detects a measured force B. The measured position C is compared with the expected position C and the measured force B is compared with the expected force B. The comparisons indicate whether the measured position C deviates from expected position C more than a threshold (not matching) or less than a threshold (matching), and whether the measured force B deviates from the expected force B more than a threshold (not matching), or less than a threshold (matching). If the measured and the expected match, the surgical robotic system determines that buckling has not occurred, and that it has occurred if they do not match.

Figures 9E, 9F:
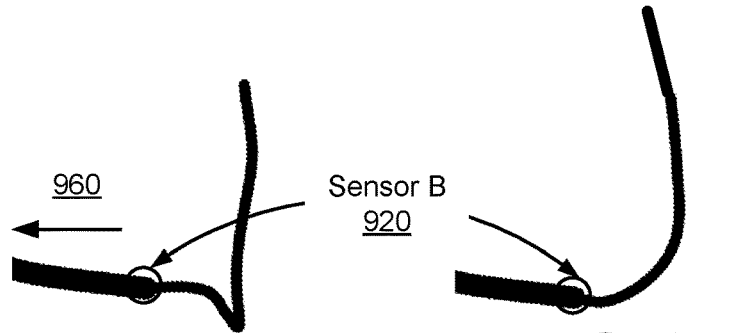

As shown in FIGS. 9E-9F, a sensor B is placed in the third sensor region (e.g., a portion of the distal sheath section). In response to a command to move the endoscope to an expected position E in the third region, the measured position E is compared with the expected position E shown in FIG. 9F. The measured position E shown in FIG. 9E has moved backward 960 indicating that the measured position E does not match the expected position E, the surgical robotic system determines buckling has occurred. The sensor B can also be a force sensor. For example, in response to a command to move the endoscope, the endoscope has an expected force C in the third region. The sensor B detects a measured force C (e.g., a friction between the third sensor region and the leader), and the measured force C is compared with the expected force C. The measured force is greater than the expected force C in FIG. 9F indicating that the measured force C does not match the expected C, the surgical robotic system determines that buckling has occurred.

Figures 9G, 9H:
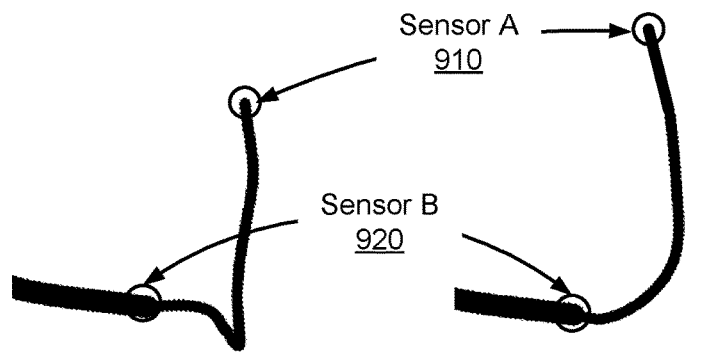

The example embodiments illustrated in this section may be variously combined with each other to provide other possible sensor setups for an endoscope, as well as buckling detection processes that use the detection of status changes in more than region at a time to identify or verify that buckling has occurred. For example, expected vs. measured data from sensor A in the first sensor region A can be combined with expected vs. measured data from sensor B in the third sensor region as shown in FIGS. 9G-H. Similar to FIGS. 9C-9D, the sensor C and the sensor D can have the same or different sensor types.

The shape of the leader (or sheath) can be detected using multiple position sensors as shown in FIGS. 9I-9J or by a shape sensing optical fiber as shown in FIGS. 9K-9L. A shape sensing optical fiber may include a segment of a fiber Bragg grating (FBG). The FBG reflects certain wavelengths of light, while transmitting other wavelengths. The surgical robotics system generates reflection spectrum data based on the wavelengths of light reflected by the FBG. The system can analyze the reflection spectrum data to generate position and orientation data of the endoscope in two or three dimensional space. In particular, as the endoscope bends, the shape sensing optical fiber embedded inside also bends. The specific wavelengths of light reflected by the FBG changes based on the shape of the shape sensing optical fiber (e.g., a "straight" endoscope is in a different shape than a "curved" endoscope). Thus, the system can determine, for example, how many degrees the endoscope has bent in one or more directions (e.g., in response to commands from the surgical robotic system) by identifying differences in the reflection spectrum data.

Endolumenal bucking is detected based on a comparison between the measured shape and the expected shape as provided by the shape sensing optical sensor or the discrete sensors. A function can be used to estimate the shape of the leader (or sheath), e.g., linear (e.g., polynomial interpolation) or non-linear interpolations (e.g., spline interpolation), curve fitting based on one more fitting functions, linear or non-linear regression analysis, or some combination thereof.

As shown in FIGS. 9K-9L, a shape sensing optical fiber 950 is placed along the leader (or sheath, not shown). For example, the shape sensing sensor can be placed in conduits with the pull wires inside the length of walls of the leader (or the sheath). The shape sensing sensor can be placed in the outside of conduits but inside the length of walls of the leader (or the sheath).

FIG. 10 is a flowchart of a general process 1000 for detecting endolumenal buckling based on a comparison between measured status and expected status according to one embodiment. A controller of a surgical robotics system, for example, the controller 120 of the surgical robotics system 100 shown in FIG. 1, uses the process 1000 to detect endolumenal buckling. The process 1000 may include different or additional steps than those described in conjunction with FIG. 10 in some embodiments, or perform steps in different orders than the order described in conjunction with FIG. 10.

The controller 120 receives 1010 sensor data generated from a first sensor placed in a portion of the endoscope located within a patient lumen, and the sensor data indicates a measured status based on an actual motion of the portion of the endoscope. The portion of the endoscope can be the three sensor regions mentioned above as shown in FIGS. 8A-8B. Examples are described in FIGS. 9A-9L. The controller 120 receives 1020 expected data describing data associated with an expected status caused by an expected motion of the endoscope. In some embodiments, the expected data is robotic command data generated from an instrument device manipulator (IDM) physically coupled to the endoscope, where the robotic command data is configured to control the IDM to cause the portion of the endoscope to move within the patient towards an expected position. The robotic command data indicates the expected status based on the expected motion. The controller 130 compares 1030 the measured status with the expected status. Responsive to the measured status deviating from the expected status more or less than an associated threshold, the controller 130 determines 1040 that the endoscope has buckled. In some embodiments, the threshold indicates a match between the measured status and the expected status.

II.A.2. Endolumenal Buckling Detection Based on Status Changes Indicated by Sensor Data In the prior section, buckling was described as being detected based on a difference between expected vs. measured behavior. This section describes how buckling can be detected on a change in endoscope state between two points in time, generally during the carrying out of a motion command by the endoscope (e.g., insertion).

FIGS. 11A-11H illustrate examples of endolumenal buckling detection based on before and after (or during) a command, according to one embodiment. Status change detection for each sensor region is similar to the examples described in FIGS. 9A-9H, with the exception that instead of using expected data and measured data to detect status change, measured data at two different points in time is used instead.

Figures 11A, 11B:
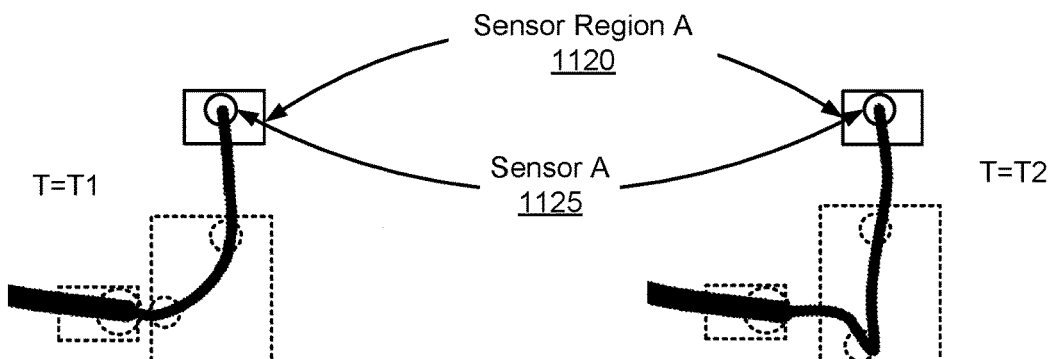
FIGS. 11A-11H illustrate examples of endolumenal buckling detection based on before and after (or during) a command, according to one embodiment.

As a first example, as shown in FIGS. 11A-B, a sensor A 1125 is placed in a sensor region A 1120 (e.g., tip of the endoscope). At $T=T_1$, the sensor A 1125 detects a measured status A (e.g., a position A, or a force A depending on sensor type of sensor A). At $T=T_2$, the sensor A 1125 detects a measured status B (e.g., a position B, or a force B). If the measured status at T1 and T2 triggers one of the thresholds of one of the status changes (e.g., increase in force, insufficient change of position) for sensor A located near the tip, the system determines that buckling has occurred.

Although a status change can be sufficient to detect buckling, in some instances the identification of two or more status changes helps determine or verify that buckling has occurred. These detected status changes may originate from different sensors of the same or different type in the same or different regions. For example, if another sensor with different type (e.g., a force sensor) is placed in the sensor region A 1120, if that other sensor also detects a corresponding status change, then it may be better determined or verified that buckling has occurred.

Figures 11C, 11D:
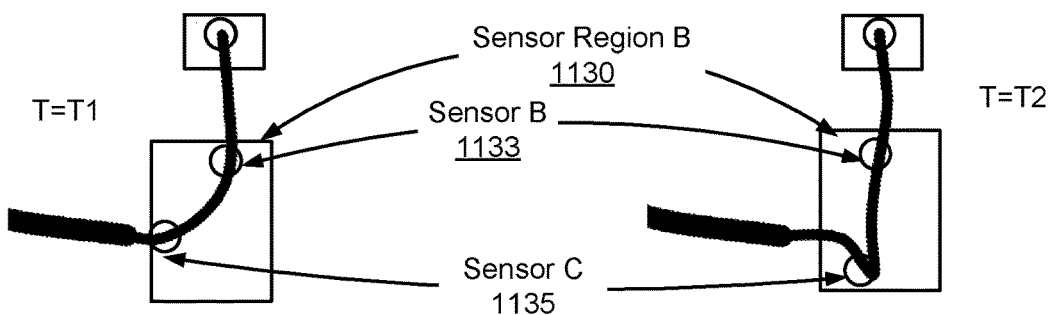
Figures 11E, 11F:
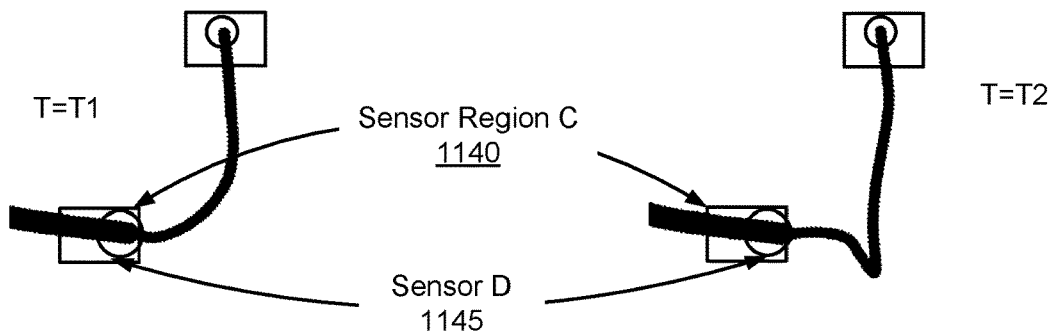
Figures 11G, 11H:
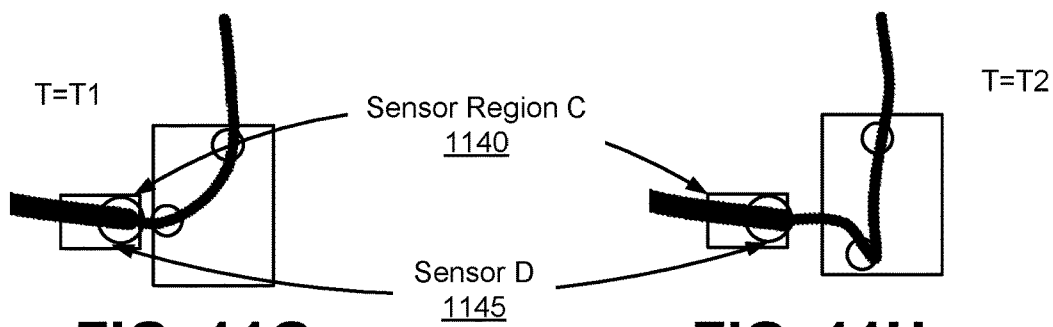

Similarly, one or more sensors, of the same sensor type, or of different sensor types can be placed in more than one sensor region to evaluate if the endoscope has undergone corresponding status changes associated with respective sensor region. By combining at least two status changes detected from different regions based on measured data at two different points in time, the system will have a better ability to detect buckling as it occurs. FIGS. 11C-11H illustrate examples of two status changes being detected in two different regions. Examples include various combinations of sensors in region A, B, and C. FIGS. 11C and 11D illustrate detecting buckling based on status changes in regions A and B. FIGS. 11E and 11F illustrate detecting buckling based on status changes in regions A and C, and FIGS. 11G and 11H illustrate detecting buckling based on status changed in regions B and C. Although not shown, buckling may be detected based on status changes in all three regions.

Figure 12:
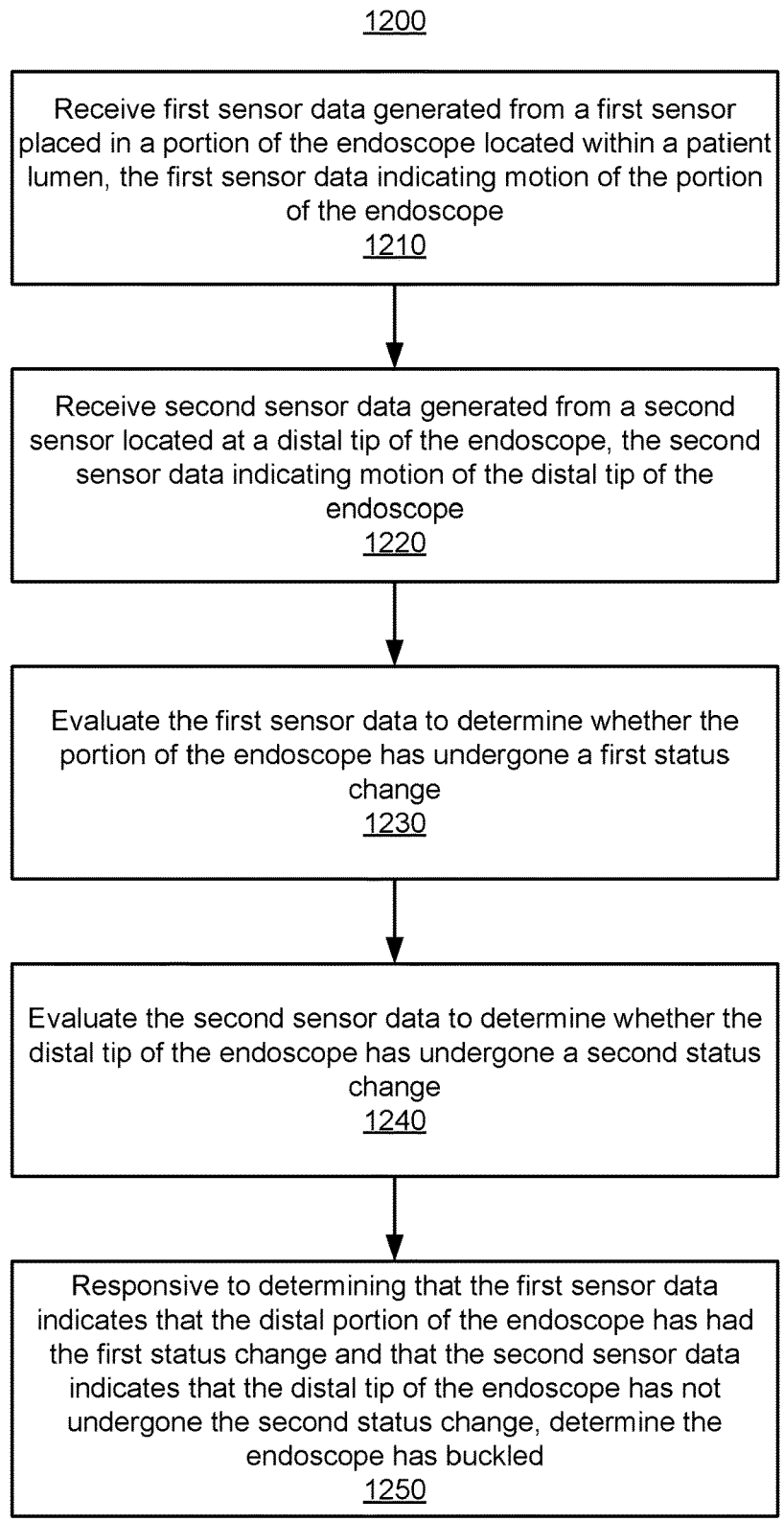
FIG. 12 is a flowchart of a process for detecting endolumenal buckling based on status changes indicated by sensor data according to one embodiment.

II.A.3 Endolumenal Buckling Detection Based on a Comparison Between Status Changes Indicated by Sensor Data and Optical Flow Data FIG. 12 is a flowchart of a process 1200 for detecting endolumenal buckling based on status changes indicated by sensor data according to one example embodiment. The process 1200 may include different or additional steps than those described in conjunction with FIG. 12 in some embodiments, or perform steps in different orders than the order described in conjunction with FIG. 12.

A controller 120 of a surgical robotics system receives 1210 first sensor data generated from a first sensor placed in a portion of the endoscope located within a patient lumen, the first sensor data indicating motion of the portion of the endoscope. In some embodiments, the first sensor is located in one of the three sensor regions (e.g., sensor regions A-C). For example, the first sensor is located in the sensor region C. Examples of the first sensor include a position sensor (e.g., EM sensor), an image sensor, a force sensor, or a resistance sensor.

The controller 120 receives 1220 second sensor data generated from a second sensor located at a distal tip of the endoscope, the second sensor data indicating motion of the distal tip of the endoscope. In some embodiments, the second sensor is an imaging device mounted on the distal tip (e.g., the imaging device 349 on the endoscope 118 in FIG. 3C). The second sensor data (also referred to as optical flow data) is images captured the imaging device. As described in Section I.C.2., the second sensor data is used to estimate motion of the endoscope based on changes between a pair of images.

The controller 120 evaluates 1230 the first sensor data to determine whether the portion of the endoscope has undergone a first status change (e.g., any type of status change mentioned above). The controller 120 evaluates 1240 the second sensor data to determine whether the distal tip of the endoscope has undergone a second status change (e.g., the tip does not move). Responsive to determining that the first sensor data indicates that the distal portion of the endoscope has had the first status change and that the second sensor data indicates that the distal tip of the endoscope has had the second status change, the controller 120 determines 1250 the endoscope has buckled.

II.B. Detecting Buckling Outside a Patient

Figure 13D:
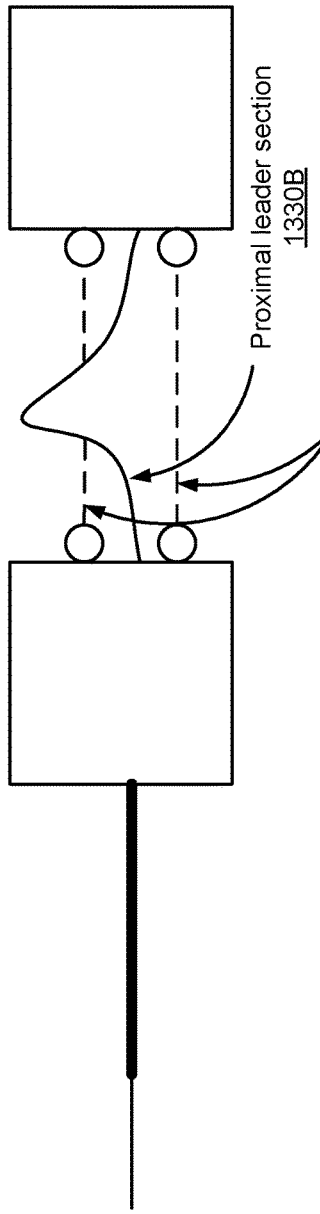

Buckling of the endoscope may occur outside a patient. For example, a buckling may occur along a proximal leader section between the leader base and sheath base. FIGS. 13A-13F are examples of detecting buckling of an endoscope outside a patient according to one embodiment. As shown in FIG. 13A, sensors 1340 are placed on both leader base 1310 and sheath base 1320. Two sensors constitute a transmitter-receiver pair. For example, the transmitter transmits a light beam 1345 of infrared light or visible light, and the receiver coaxial with the transmitter or adjacent to the transmitter detects the light beam 1345. The transmitter 1340 is placed opposite to the receiver 1343 as shown in FIG. 13A, or vice versa.

Figure 13E:
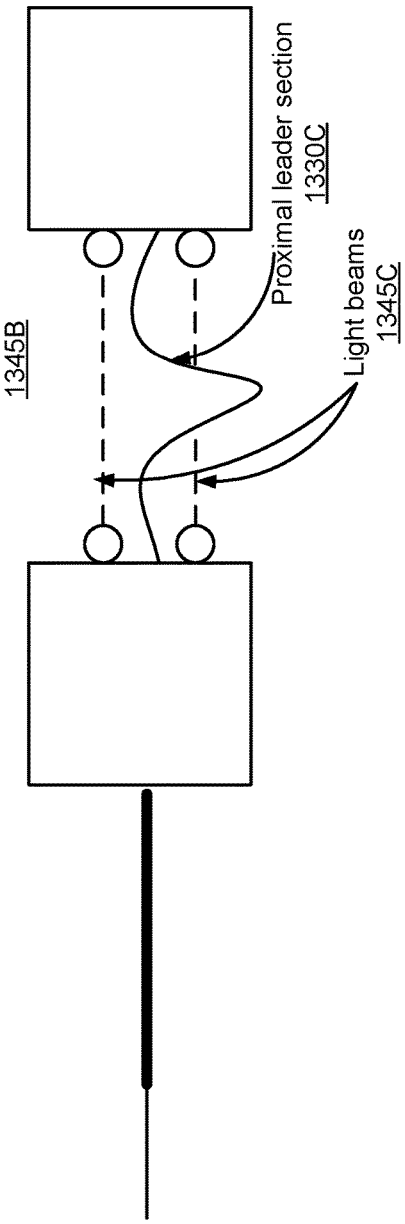
Figure 13F:
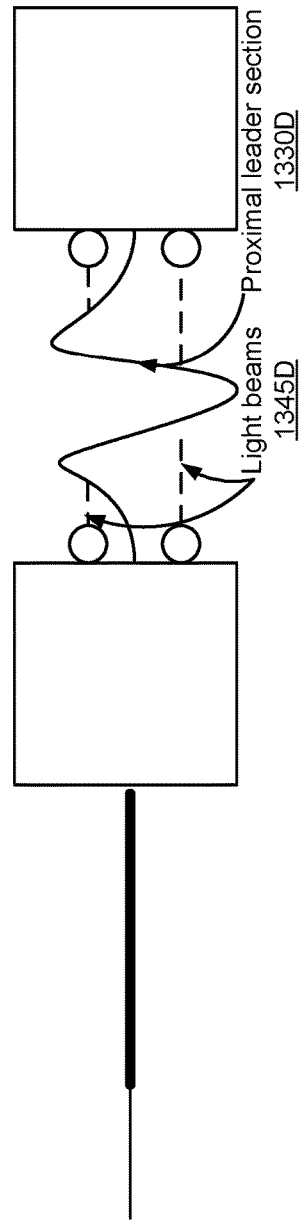

The transmitter 1340 is placed around an exit 1315 of the proximal leader section 1330 on the leader base 1310 at a distance 1350 between the transmitter and the exit. The corresponding receiver 1343 is placed around an entrance 1325 of the proximal leader section 1330 on the sheath base 1320 at the same distance between the receiver and the entrance 1325. The distance 1350 is within a threshold, representing a suitable distance range for detecting buckling. When buckling occurs, as shown in FIGS. 13D-13F, a buckled portion of the proximal leader section fully or partially blocks the light beam, and no light signal is detected by the receiver, or the light signal detected by the receiver is reduced accordingly.

The transmitter-receiver pair may be placed on the same side of the proximal leader section, as shown in FIG. 13C. For example, the transmitter-receiver pair is placed around the exit 1315 and a reflector 1360 is placed around the entrance 1325 to reflect a light beam transmitted from the transmitter to the corresponding receiver. As shown in FIG. 13C, the transmitter 1340 is placed at a distance A 1350 and a receiver 1343 is placed at a distance B 1355. The distances A 1350 and B 1355 are within the threshold for detecting buckling. When buckling occurs, a buckled portion of the proximal leader section fully or partially block the light beam, and no light signal is detected by the receiver, or the light signal detected by the receiver is reduced accordingly.

More than one set of transmitter-receiver pairs may be used to detect buckling at different directions. For example, multiple transmitters are placed around the exit 1315 between each transmitter and the exit 1315. The multiple transmitter-receiver pairs may be distributed to generate parallel light beams from each other, or they may be distributed to generate crossed light beams to better cover the cylindrical surface area around the endoscope. In some embodiments, the transmitted light beams are focused light, such as laser beams, how they may also be dispersed in nature and matched with receivers configured to receive the type of light emitted.

FIG. 14 is a flowchart of a process 1400 for detecting buckling outside a patient based using transmitter-receiver pairs according to one embodiment. A controller of a surgical robotics system, for example, the controller 120 of the surgical robotics system 100 shown in FIG. 1, uses the process 1400 to detect buckling. The process 1400 may include different or additional steps than those described in conjunction with FIG. 14 in some embodiments, or perform steps in different orders than the order described in conjunction with FIG. 14.

The controller 120 provides 1410 one or more commands from the surgical robotic system 100 to one or more actuators, for example, the sheath base 1320 and leader base 1310 shown in FIGS. 13A-13F, to move the endoscope 118 for a surgical procedure.

The controller 120 receives receiver data generated from at least one transmitter-receiver pair placed along a length of the endoscope outside the patient, the transmitter-receiver pair configured to transmit a light beam from a transmitter to a receiver, the receiver data indicating whether the receiver has had received light beam transmitted from the transmitter. For example, the transmitter is placed on the sheath base and the receiver is placed on the leader base as shown in FIG. 13B and FIGS. 13D-13F.

Responsive to the receiver data indicating that the light from the transmitter has been blocked, the controller 120 determines that the endoscope has buckled.

Figure 15:
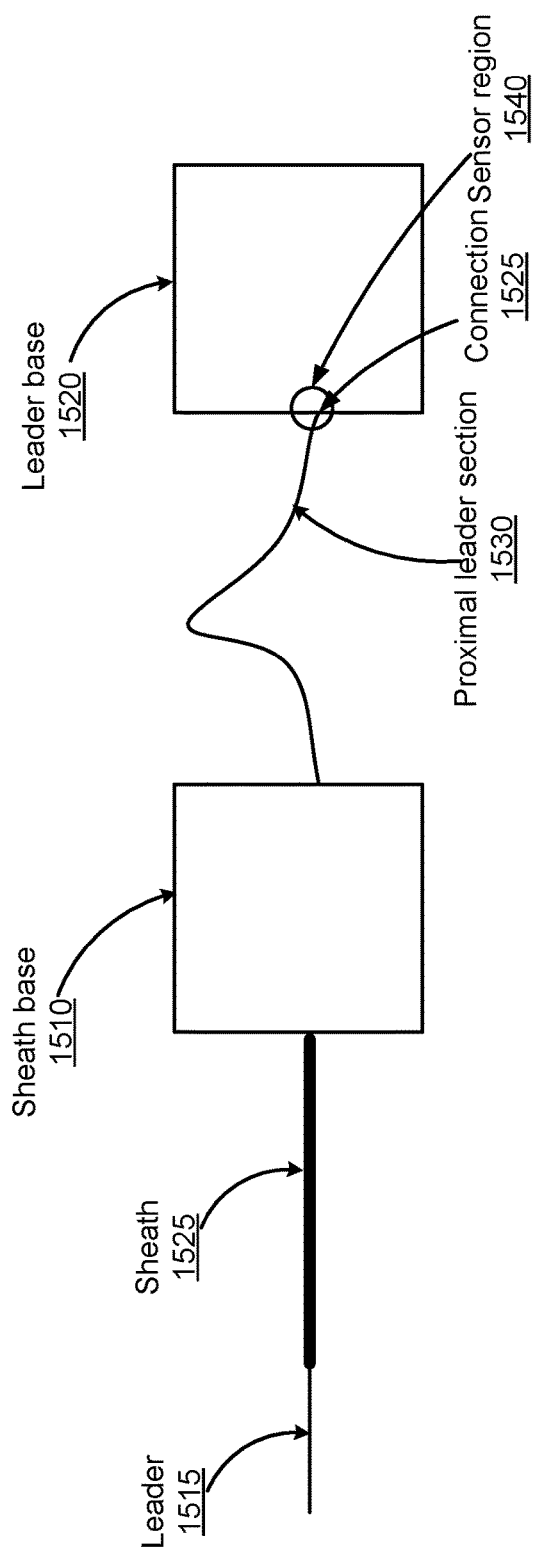
FIG. 15 illustrates another example of detecting buckling of an endoscope outside a patient according to one embodiment.

Rather than using optical sensors, in an alternate implementation one or more force sensors can be placed in a sensor region around an entrance on a sheath base to detect buckling outside the patient. FIG. 15 illustrates another example of detecting buckling of an endoscope outside a patient according to one embodiment. As shown in FIG. 15, the sensor region 1540 located around the connection 1525 of the leader base 1520 is in contact with a proximal leader section 1530. When a buckling along the proximal leader section occurs, force between the sensor and contacted portion of the proximal leader section is increased. Sensors, include strain gauges or load cells in rigid connection with the proximal leader section 1530. Examples of strain configuration are described in U.S. application Ser. No. 14/542,403, filed on Nov. 14, 2014, published as U.S. Pat. Pub. No. US 2015/0119638, entitled "INSTRUMENT DEVICE MANIPULATOR WITH TENSION SENSING APPARATUS," the full disclosure of which is incorporated herein by reference.

III. Other Buckling Considerations

The controller 120 generates feedback for a user indicating that the endoscope has buckled and provides the feedback to users. For example, the controller 120 generates a message or a warning indicating that the endoscope has buckled. This message or warning may be provided for display on a graphical user interface (GUI), for example one or more monitors being used by the operator to control the operation. The controller 120 can also generate a recommendation to users. To do this, the controller 120 determines one or more modifications to a command to move the endoscope. The modification is based on at least in part on the sensor data. For example, the controller 120 may adjust the command to smooth the buckled portion of the endoscope. Examples of command include moving the endoscope backward, adjusting movement of the tip, adjusting insertion force provided by the IDM, another suitable command that adjusts endoscope's movements, stopping movement of the endoscope, or some combination thereof.

Although the above description is generally described with respect to examples that focus on the leader, endolumenal buckling may also occur along the sheath. Similar methods to those described above for the leader can also be applied to the sheath. For example, the first sensor region can be the tip of the endoscope or a small region around the end of the sheath. The second sensor region can be a portion of the sheath. The third sensor region may be omitted, or interpreted as another region along the sheath located further from the sheath tip than the second region.

IV. Endoscope Insertion Using Adaptive Insertion Force Threshold

As mentioned earlier, a surgical robotic system 100 uses one or more robotic arms 102 to control an endoscope 118 in a patient for surgical procedures. The robotic arms apply an insertion force to insert and advance the endoscope to an operative site. As the endoscope is advanced, the force required to further advance the endoscope will change over time depending on a variety of factors including the location of the operative site, the path taken within the patient cavity to get there, the size of the endoscope, etc. Correspondingly, depending at least on the path chosen, the amount of force that may be safely applied without injuring the patient lumen will vary. For example, within a single lung network in a patient, a single force threshold limit that may be set to avoid injury is not applicable for all lobes. Generally the upper lobes need more insertion force than the lower lobes due to bending in the endoscope to enter those areas. As such, a dynamic force insertion threshold is needed to allow operations to be performed safely while still preventing the application of a level of force above that dynamic threshold.

IV.A. Determining an Adaptive Insertion Force Threshold

As described herein, the surgical robotics system makes use of an adaptive insertion force threshold to regulate insertion force for different locations within a patient's lumen to avoid unsafe further insertion to the patient. The adaptive insertion force threshold is determined based on endoscopic data and patient data.

The endoscopic data describes data associated with the endoscope during a navigation. Examples of the endoscopic data include a friction force between a sheath and a leader, a friction force between the sheath and internal anatomy, a friction force between the leader and the internal anatomy, a current location of the endoscope, a target location of the endoscope, insertion length of the sheath, insertion length of the leader, a distance between the sheath and the leader (e.g., a difference between the insertion length of the sheath and the insertion length of the leader, a distance between a distal end of the sheath and the tip of the endoscope), motion of the leader (e.g., translation, rotation, blending, etc.), motion of the sheath (e.g., translation, rotation, blending, etc.), motion of the tip (e.g., translation, rotation, deflection, etc.), a contact interaction between the tip and a portion of a tissue within a patient (e.g., contacting force), force on the leader within the patient, force on the sheath within the patient, force on the tip, another suitable data affecting movements of the endoscope, or some combination thereof.

The endoscope data can be obtained from one or more sensors placed on the endoscope. For example, a position sensor or an image sensor on the tip of the endoscope can obtain a current location of the endoscope, and motions of the tip. A force sensor on the tip can obtain a contacting force between the tip and a portion of a tissue within a patient, or other types of force between the tip and contacting tissue (e.g., friction, pressure, etc.). One or more sensors of different sensor types (e.g., position sensor, force sensor, shape sensor, etc.) can be placed on a portion of leader or sheath to detect length, motions, or different types of force associated with the leader or the sheath. Examples are described in Section II. above.

Patient data describes associated with a patient inserted by the endoscope. Examples of patent data include medical data (e.g., medical diagnosis, medical treatment, disease, medical history, other suitable medical data affecting navigation, or some combination thereof), general information (e.g., gender, age, habit, etc.), or some combination thereof. The patient data may be stored in a database included in and accessible by the robotic surgical system.

As introduced above, the adaptive insertion force threshold is determined by a function associated with the endoscopic data and patient data. In a first embodiment, the adaptive insertion force threshold is determined based on a nonlinear function associated with a relationship among an insertion force threshold, endoscopic data and patient data. By inputting the endoscopic data and patient data, the function generates an insertion force threshold. In a second embodiment, the adaptive insertion force threshold is determined based on optimizing a metric. The metric accounts for an effect of applying an insertion force within a safety range. The safety range describes a range that the insertion force doesn't damage contacting tissues or organs within the patient. For example, an optimization function is used to find a maximum insertion force within the safety range. In a third embodiment, the insertion force threshold is determined based on a machine learning algorithm. For example, by historical endoscope data and patient data regarding prior similar operations may be passed as a training data set into a machine learning model, and various parameters for determining the insertion force threshold is generated. The parameters may be the same parameters as there are types of patient and endoscopic data introduced above, however additional or different parameters may also be used. In some embodiments, patient data can be used as constraints to functions in above embodiments. For example, if a patient has an asthma disease, the walls of airways become inflamed and oversensitive. Consequently, the force insertion threshold may be set to a lower value than it would be for a patient without asthma.

The insertion force threshold may also be determined based on a look-up table. The look-up table includes data describing a plurality of insertion force thresholds having various characteristics. For example, the look-up table describes a plurality of insertion force thresholds associated with different endoscope's locations of a patient or of a group of patients. The look-up table may be obtained by statistical analysis of various endoscope data and various patient data, machine learning applied to various endoscope data and various patient data, data mining of various endoscope data and various patient data, or by any other suitable method. Various types of look-up tables may be stored by the surgical robotics system in different embodiments. Example types of look-up tables stored by the controller include: a probability distribution of a likelihood of insertion force thresholds relative to different locations of the endoscope, clusters of insertion force thresholds having different characteristics, or other suitable information (e.g., numbers, density, classification). In one example, the look-up table is obtained from application of patients having different characteristics (e.g., gender, age) by one or more robotic surgical systems. The look-up table may identify characteristics of insertion force thresholds obtained from a patient or from a threshold number or percentage of patients. In some embodiments, a look-up table is generated for each patient. Based on patient data and endoscopic data, an insertion force threshold can be determined. In some embodiments, a look-up table is generated for different types of patients.

Figure 16A:
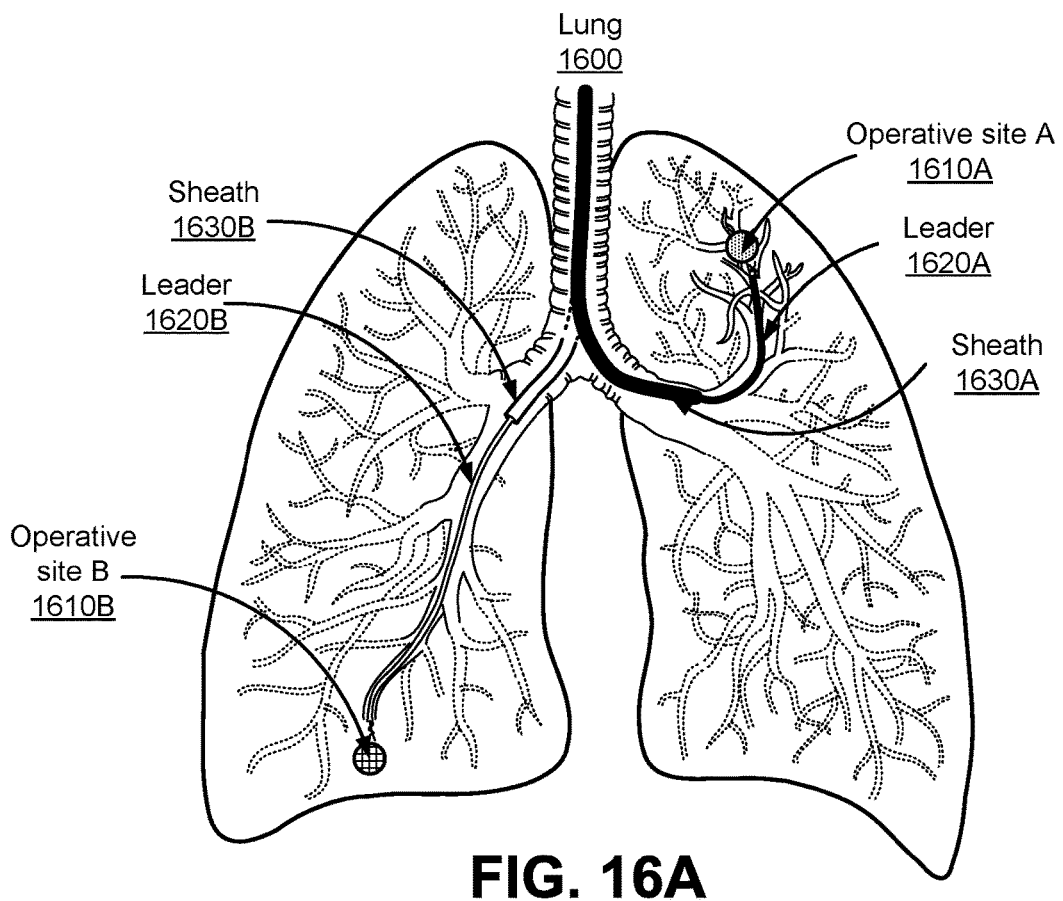
FIGS. 16A-C illustrate examples of adaptive insertion force thresholds used at different locations of an endoscope with different patients according to an embodiment.
Figure 16B:
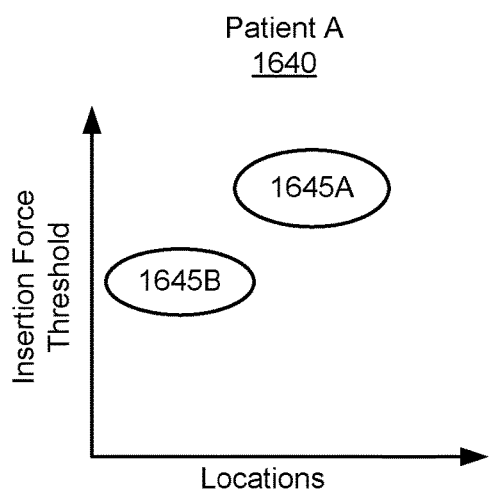
Figure 16C:
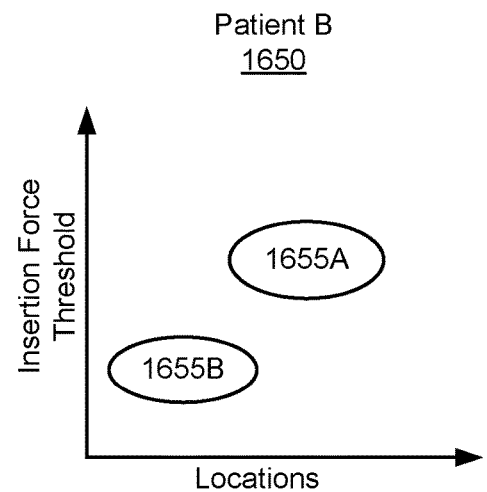

FIGS. 16A-C illustrate examples of adaptive insertion force thresholds used at different locations of an endoscope with different patients according to an embodiment. FIG. 16A shows two examples of inserting an endoscope to an operative site. The first example shows the endoscope is inserted into an operative site A 1610A located in the left upper lobe of lung 1600. The second example shows the endoscope is inserted into an operative site B 1610B located in the right lower lobe of the lung 1600. As shown in FIG. 16A, the two examples have different endoscope data. For example, the two examples have different locations of the endoscope, different insertion lengths of the sheath 1630, different lengths of the leader 1620, different distances between the sheath 1630 and the leader 1620, different motions of the endoscope (e.g., the leader 1620A bends more than the leader 1620B), etc. Different endoscope data results in different insertion force thresholds. For example, the first example needs more insertion force to overcome a force (e.g., torque, friction) generated due to bending. Moreover, different patients may have different insertion force thresholds at the same operative site.

As shown in FIGS. 16B-16C, the insertion force threshold to allow insertion of the endoscope while preventing injury may not be a value that can be precisely determined based on available data. Consequently, the system may instead determine an insertion force threshold with size determined based on any of the techniques described previously. An insertion force threshold region indicates a probability distribution (e.g., a cluster or density) of a likelihood of insertion force threshold being safe (i.e., not harming the patient) relative to a location of the endoscope (e.g., a location proximal to the operative site), or statistical data of insertion force threshold relative to the location of the endoscope. In some embodiments, the insertion force threshold region indicates a plurality of possible insertion force thresholds relative to a plurality of possible locations during a navigation to an operative site.

FIGS. 16B-16C illustrate region 1645A from a first patient 1640 and an insertion force threshold region 1655A from a second patient 1650, both associated with operative site A 1610A, and similar insertion force threshold regions 1645B and 1655B for the first and second patients with respect to a second operative site 1610B. These figures illustrate the possible differences between threshold regions between patients for similar operative sites and procedures, and also the variance between operative sites for similar procedures.

In some embodiments, the surgical robotic system actively determines the insertion force threshold during a navigation. In some embodiments, the insertion force thresholds may be pre-determined and tagged to different portions of a pre-operative model as part of a robotic pre-operative planning stage.

The surgical robotic system compares the insertion force with the determined insertion force threshold. The insertion force can be detected by one or more force sensors coupled to a robotic arm of the surgical robotic system. When the insertion force is approaching the insertion force threshold within a predefined range or approaches the insertion force threshold, the surgical robotic system sends a visual and/or audio feedback to a user via the system GUI. For example, a warning indicating that the insertion force is very close to the insertion force threshold, or approaches the insertion force threshold. Different colors, such as green, yellow, and red, may be used to indicate relative distance to the insertion force threshold. In other embodiments, upon reaching the insertion force threshold, the surgical robotic system generates a recommendation to the user. To do this, the surgical robotic system determines one or more modifications to a command to insert the endoscope. The modification is based on at least in part on the endoscopic data and patient data. Examples of command includes ceasing one or more insertion forces from the surgical robotic system, reducing the insertion force, another suitable command that adjusts insertion force, or some combination thereof.

IV.B. Inserting an Endoscope Using an Adaptive Insertion Force Threshold

Figure 17:
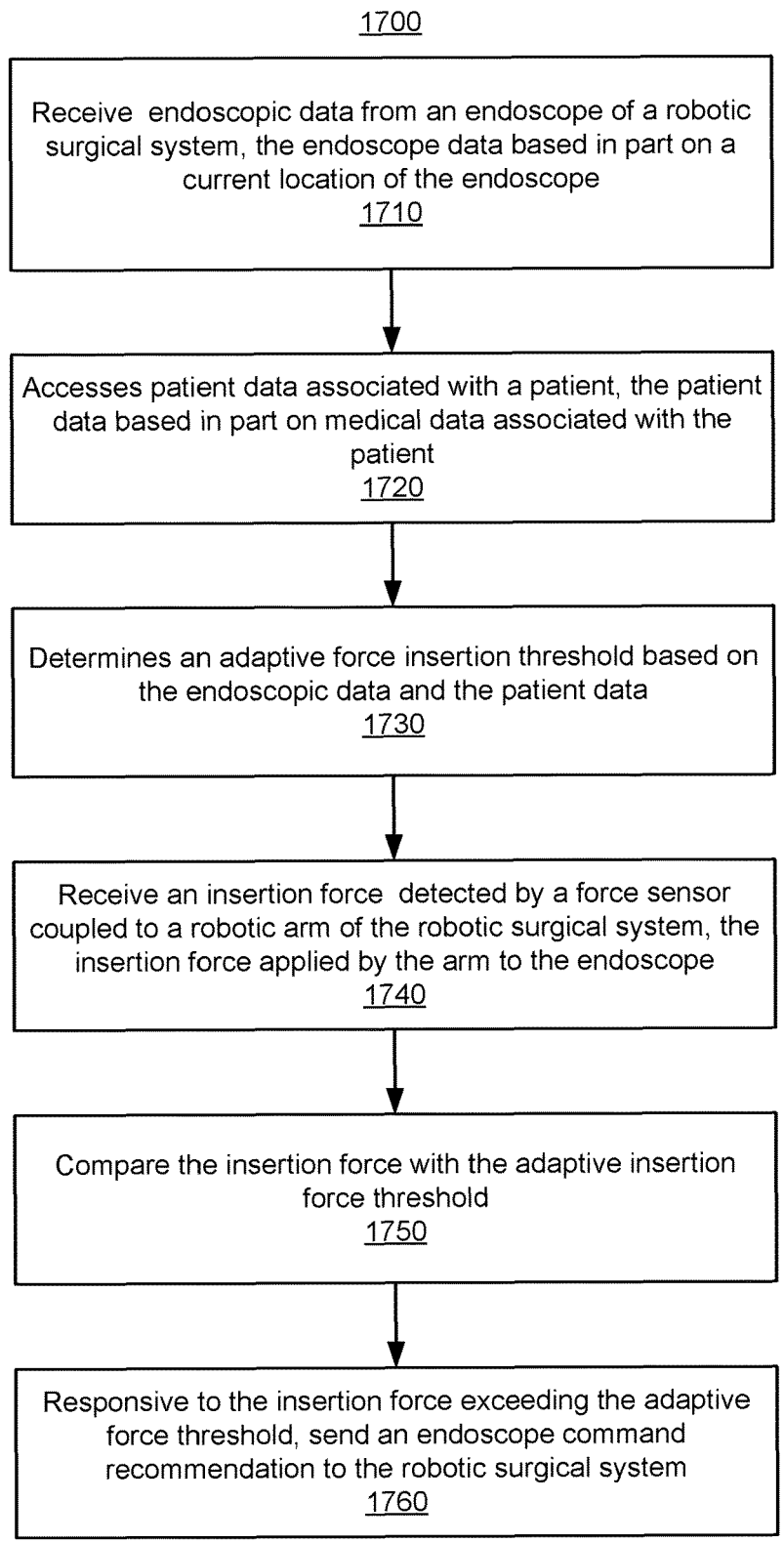
FIG. 17 is a flowchart of a process for inserting an endoscope using an adaptive insertion force threshold according to one embodiment.

FIG. 17 is a flowchart of a process 1700 for inserting an endoscope using an adaptive insertion force threshold according to one embodiment. A controller of a surgical robotics system, for example, the controller 120 of the surgical robotics system 100 shown in FIG. 1, uses the process 1700 to insert the endoscope using the adaptive insertion force threshold. The process 1700 may include different or additional steps than those described in conjunction with FIG. 17 in some embodiments, or perform steps in different orders than the order described in conjunction with FIG. 17.

The controller 120 receives 1710 endoscopic data from an endoscope of a robotic surgical system, the endoscope data based in part on a current location of the endoscope. For example, the controller 120 can obtain sensor data as endoscopic data from one or more sensors placed on the endoscope (e.g., sheath, leader, or tip).

The controller 120 accesses 1720 patient data associated with a patient, the patient data based in part on medical data associated with the patient. For example, the controller 120 can access a patient data database stored in the robotic surgical system. The controller 120 can obtain the patient data by accessing one or more external databases via a network.

The controller 120 determines 1730 an adaptive force insertion threshold based on the endoscopic data and the patient data. For example, the controller 120 determines the adaptive force insertion threshold based on one or more functions or models, a look-up table, or based on insertion force threshold region.

The controller 120 receives 1740 an insertion force detected by one or more force sensors coupled to a robotic arm of the robotic surgical system, the insertion force applied by the arm to the endoscope. For example, one or more force sensors can be placed on one or more arm segments of the robotic arm, one or more joints of the robotic arm, a connection between the robotic arm with an IMD, other suitable location affecting movement of the robotic arm, or some combination thereof.

The controller 120 compares 1750 the insertion force with the adaptive insertion force threshold. Responsive to the insertion force exceeding the adaptive force threshold, the controller 120 sends 1760 an endoscope command recommendation to the robotic surgical system. For example, if the insertion force exceeds the adaptive force threshold, the controller 120 sends a message or a warning indicating that the insertion force exceeds the insertion force threshold. The controller 120 determines one or more modifications to a command to adjust the insertion force.

V. Alternative Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method for detecting buckling of a medical instrument comprising an elongate body, the method comprising:
    directing a command to move an elongate body;
    receiving sensor data generated from a first sensor placed in a first portion of the elongate body, the sensor data comprising information regarding a first measured status of the first portion of the elongate body;
    determining a first expected status of the first sensor from command data useable to control a manipulator coupled to the elongate body to effect movement of the elongate body;
    comparing the first measured status with the first expected status; and
    responsive to the first measured status deviating from the first expected status relative to a first associated threshold, determining that the elongate body has buckled.

2. The method of claim 1, wherein the elongate body comprises at least one of a catheter and an endoscope.

3. The method of claim 1, wherein the elongate body comprises of a leader and a sheath, the leader being telescopically disposed within the sheath.

4. The method of claim 3, wherein the first portion of the elongate body comprises at least one of:
    a first region covering a volume near a tip of the leader;
    a second region covering a portion of the leader in a range from a distal end of the sheath to an edge of the first region; and
    a third region covering the distal end of the sheath where the leader extending from as well as a portion of the sheath proximal to its distal end.

5. The method of claim 3, wherein the first portion of the elongate body comprises at least one of:
    a first region covering a volume near an end of the sheath, wherein the end of the sheath is where the leader extends from;
    a second region covering a first portion of the sheath in a range from a first location of the sheath to an edge of the first region; and
    a third region covering a second portion of the sheath in a range from a second location of the sheath to an edge of the second region, wherein the second location is further from the first region than the second location.

6. The method of claim 1, wherein the first sensor is coupled to at least one of:
    a portion of an outer surface of the elongate body;
    a portion of a wall of the elongate body;
    a portion of an inner surface of a lumen within the elongate body;
    a portion of an inner surface of a conduit within the elongate body; and
    a portion of a pull wire within a lumen within the elongate body.

7. The method of claim 1, wherein the first sensor comprises a position sensor wherein the first measured status and the first expected status represent determinations of a change in position of the elongate body, and wherein responsive to the first measured status deviating from the first expected status less than the first threshold, determining that the elongate body has buckled.

8. The method of claim 1, wherein the first sensor comprises a force sensor wherein the first measured status and the first expected status represent determinations of force experienced by the force sensor, and wherein responsive to the first measured status deviating from the first expected status more than the first threshold, determining that the elongate body has buckled.

9. The method of claim 1, wherein the first sensor comprises an image sensor wherein the first measured status and the first expected status represent determinations of movement of the elongate body based on at least one image captured by the image sensor, and wherein responsive to the first measured status deviating from the first expected status less than the first threshold, determining that the elongate body has buckled.

10. The method of claim 1, wherein the first sensor comprises a shape sensor wherein the first measured status and the first expected status represent determination of bending by the elongate body, and wherein responsive to the first measured status deviating from the first expected status more than the first threshold, determining that the elongate body has buckled.

11. The method of claim 10, wherein the shape sensor comprises an optical fiber shape sensing sensor or wherein the shape sensor comprises a plurality of position sensors, wherein the plurality of position sensors generates a plurality of discrete positions able to be fitted by a function to estimate a shape.

12. The method of claim 1, wherein the command data is generated from a robotic manipulator physically coupled to the elongate body, wherein the command data is configured to control the robotic manipulator to cause the first portion of the elongate body to move towards an expected position.

13. The method of claim 1, the method further comprises:
receiving sensor data generated from a second sensor placed in a second portion of the elongate body, the second sensor data comprising information regarding a second measured status of the second portion of the elongate body;
determining a second expected status of the second sensor from the command data useable to control the manipulator coupled to the elongate body to effect movement of the elongate body;
comparing the second measured status with the second expected status; and
responsive to the first measured status deviating from the first expected status relative to a first associated threshold and the second measured status deviating from the second expected status relative to a second associated threshold, determining that the elongate body has buckled.

14. The method of claim 1, further comprising:
generating feedback for a user indicating that the elongate body has buckled, wherein generating feedback for the user comprises at least one of:
determining one or more modifications to a recommendation to move the endoscope,
generating a message indicating that the elongate body has buckled, and
generating a warning indicating that the elongate body has bucked; and
providing the feedback to the user.

15. The method of claim 14, wherein the recommendation comprises at least one of:
retracting the elongate body;
adjusting movement of a tip of the elongate body;
adjusting insertion force provided by a robotic manipulator; and
stopping movement of the elongate body.

16. A robotic system, comprising:
a medical instrument comprising an elongate body;
a first sensor placed in a first portion of the elongate body; and
a controller configured to:
direct a command to move the elongate body,
receive sensor data generated from the first sensor, the sensor data comprising information regarding a first measured status of the first portion of the elongate body,
determine a first expected status of the first sensor from command data useable to control a manipulator coupled to the elongate body to effect movement of the elongate body,
compare the first measured status with the first expected status; and
responsive to the first measured status deviating from the first expected status relative to a first associated threshold, determine that the elongate body has buckled.

17. The system of claim 16, wherein the elongate body comprises of at least one of a catheter and an endoscope.

18. The system of claim 16, wherein the elongate body comprises of a leader and a sheath, the leader being telescopically disposed within the sheath.

19. The system of claim 18, wherein the first portion of the elongate body comprises at least one of:
a first region covering a volume near a tip of the leader;
a second region covering a portion of the leader in a range from a distal end of a sheath of the elongated body within the patient to an edge of the first region; and
a third region covering the distal end of the sheath where the leader extending from as well as a portion of the sheath proximal to its distal end.

20. The system of claim 18, wherein the first portion of the elongate body comprises at least one of:
a first region covering a volume near an end of the sheath;
a second region covering a first portion of the sheath in a range from a first location of the sheath within the patient to an edge of the first region; and
a third region covering a second portion of the sheath in a range from a second location of the sheath to an edge of the second region, wherein the second location is further from the first region than the second location.

21. The system of claim 16, wherein the first sensor is coupled to at least one of:
a portion of an outer surface of the elongate body;
a portion of a wall of the elongate body;
a portion of an inner surface of a lumen inside the elongate body;
a portion of an inner surface of a conduits inside the elongate body; and
a portion of a pull wire of the elongate body.

22. The system of claim 16, wherein the first sensor comprises a position sensor wherein the first measured status and the first expected status represent determinations of a change in position of the elongate body, and wherein responsive to the first measured status deviating from the first expected status less than the first threshold, determining that the elongate body has buckled.

23. The system of claim 16, wherein the first sensor comprises a force sensor wherein the first measured status and the first expected status represent determinations of force experienced by the force sensor, and wherein responsive to the first measured status deviating from the first expected status more than the first threshold, determining that the elongate body has buckled.

24. The system of claim 16, wherein the first sensor comprises an image sensor wherein the first measured status and the first expected status represent determinations of movement of the elongate body based on at least one image captured by the image sensor, and wherein responsive to the first measured status deviating from the first expected status less than the first threshold, determining that the elongate body has buckled.

25. The system of claim 16, wherein the first sensor comprises a shape sensor wherein the first measured status and the first expected status represent determination of bending by the elongate body, and wherein responsive to the first measured status deviating from the first expected status more than the first threshold, determining that the elongate body has buckled.

26. The system of claim 22, wherein the shape sensor comprises an optical fiber shape sensing sensor, or wherein the shape sensor comprises a plurality of position sensors, wherein the plurality of position sensors generates a plurality of discrete positions able to be fitted by a function to estimate a shape.

27. The system of claim 16, wherein the command data is generated from a robotic manipulator coupled to the instrument, wherein the command data is configured to control the manipulator to cause the portion of the elongate body to move towards an expected position.

28. The system of claim 16, the system further comprising:
   a second sensor placed in a second portion of the elongate body;
   the controller further configured to:
      receive sensor data generated from the second sensor, the second sensor data comprising information regarding a second measured status of the second portion of the elongate body;
      determine a second expected status of the second sensor from the command data useable to control the manipulator coupled to the elongate body to effect movement of the elongate body
      compare the second measured status with the second expected status, and
      responsive to the first measured status deviating from the first expected status relative to a first associated threshold and the second measured status deviating from the second expected status relative to a second associated threshold, determine that the elongate body has buckled.

29. The system of claim 16, wherein the controller is further configured to:
   generate feedback for a user indicating that the elongate body has buckled, wherein generating feedback for the user comprises at least one of:
      determining one or more modifications to a recommendation to move the elongate body,
      generating a message indicating that the elongate body has buckled, and
      generating a warning indicating that the elongate body has bucked; and
   provide the feedback to the user.

30. The system of claim 29, wherein the recommendation comprises at least one of:
   retracting the elongate body;
   adjusting movement of a tip of the elongate body;
   adjusting insertion force provided by a robotic manipulator; and
   stopping movement of the elongate body.

* * * * *